United States Patent
Paulus et al.

(10) Patent No.: US 9,930,102 B1
(45) Date of Patent: Mar. 27, 2018

(54) METHOD AND SYSTEM FOR USING EMOTIONAL STATE DATA TO TAILOR THE USER EXPERIENCE OF AN INTERACTIVE SOFTWARE SYSTEM

(71) Applicant: Intuit Inc., Mountain View, CA (US)

(72) Inventors: Wolfgang Paulus, Ramona, CA (US); Luis Felipe Cabrera, Bellevue, WA (US); Mike Graves, Sunnyvale, CA (US)

(73) Assignee: Intuit Inc., Mountain View, CA (US)

( * ) Notice: Subject to any disclaimer, the term of this patent is extended or adjusted under 35 U.S.C. 154(b) by 320 days.

(21) Appl. No.: 14/671,054

(22) Filed: Mar. 27, 2015

(51) Int. Cl.
*H04L 29/08* (2006.01)

(52) U.S. Cl.
CPC ..................... *H04L 67/10* (2013.01)

(58) Field of Classification Search
CPC ........................................................ H04L 29/08
See application file for complete search history.

(56) References Cited

U.S. PATENT DOCUMENTS

| | | | |
|---|---|---|---|
| 7,412,708 B1 | 8/2008 | Khan et al. | |
| 8,683,348 B1 | 3/2014 | Blank et al. | |
| 8,799,157 B1 | 8/2014 | Weisman et al. | |
| 8,806,444 B1 | 8/2014 | Podgorny et al. | |
| 8,903,176 B2 * | 12/2014 | Hill | G06K 9/46 382/195 |
| 9,098,109 B2 | 8/2015 | Lappalainen et al. | |
| 9,330,239 B2 * | 5/2016 | Koduri | G06F 19/3481 |
| 9,444,824 B1 * | 9/2016 | Balazs | H04L 63/105 |
| 2002/0199166 A1 | 12/2002 | Volcani et al. | |
| 2005/0091487 A1 | 4/2005 | Cross et al. | |
| 2006/0150243 A1 | 7/2006 | French et al. | |
| 2006/0218506 A1 | 9/2006 | Srenger et al. | |
| 2008/0276186 A1 * | 11/2008 | Feduszczak | G06F 9/4443 715/762 |
| 2009/0002178 A1 | 1/2009 | Guday et al. | |
| 2009/0172100 A1 | 7/2009 | Callanan et al. | |
| 2012/0011477 A1 * | 1/2012 | Sivadas | G06F 3/015 715/866 |
| 2012/0059785 A1 | 3/2012 | Pascual et al. | |
| 2013/0124496 A1 | 5/2013 | Edgar et al. | |
| 2013/0152000 A1 * | 6/2013 | Liu | G06F 9/44 715/765 |
| 2013/0232207 A1 | 9/2013 | Westphal | |
| 2013/0325948 A1 | 12/2013 | Chen et al. | |
| 2014/0168279 A1 | 6/2014 | Huang | |

(Continued)

*Primary Examiner* — David Choi
(74) *Attorney, Agent, or Firm* — Hawley Troxell Ennis & Hawley LLP; Philip McKay

(57) ABSTRACT

Emotional state data is used to tailor the user experience of an interactive software system, by monitoring and obtaining data about a user's emotional state. The resulting emotional state data is analyzed and used to dynamically modify the user's experience by selecting user experience components based on the analysis of the user's emotional state data. In this way, different types of user experience components can be utilized to provide the user with an individualized user experience that is adapted to the user's emotional state. Different types of user experience components can be utilized to adjust the user experience to adapt to the user's new emotional state, prevent the user from entering an undesirable emotional state, and/or encourage the user to enter into a desirable emotional state.

45 Claims, 3 Drawing Sheets

(56) References Cited

U.S. PATENT DOCUMENTS

| | | |
|---|---|---|
| 2014/0289034 A1 | 9/2014 | Wu |
| 2014/0324749 A1 | 10/2014 | Peters et al. |
| 2014/0325379 A1 | 10/2014 | McDevitt et al. |
| 2015/0040026 A1* | 2/2015 | Sergunin ................. H04L 67/22 715/745 |
| 2015/0046436 A1 | 2/2015 | Li et al. |
| 2016/0048274 A1 | 2/2016 | Rosenberg |
| 2016/0066829 A1 | 3/2016 | Sales et al. |

* cited by examiner

METHOD AND SYSTEM FOR USING EMOTIONAL STATE DATA TO TAILOR THE USER EXPERIENCE OF AN INTERACTIVE SOFTWARE SYSTEM

BACKGROUND

Interactive software systems are diverse and valuable tools, providing services that were either never before available, or were previously available only through interaction with a human professional. For example, an interactive software system may provide tax preparation or financial management services. Prior to the advent of interactive software systems, a user would be required to consult with a tax preparation or financial management professional for services and the user would be limited, and potentially inconvenienced, by the hours during which the professional was available for consultation. Furthermore, the user might be required to travel to the professional's physical location. Beyond the inconveniences of scheduling and travel, the user would also be at the mercy of the professional's education, skill, personality, and varying moods. All of these factors resulted in a user vulnerable to human error and variations in human ability and temperament.

Some interactive software systems provide services that human professionals are not capable of providing, and even those interactive software systems providing services similar to those historically provided by human professionals offer many benefits: the interactive software system does not have limited working hours, is not geographically limited, and is not subject to human error or variations in human ability or temperament. Although interactive software systems represent a potentially flexible, highly accessible, and affordable source of services, they do have several significant shortcomings. For example, unlike professionals providing services, traditional interactive software systems cannot detect, much less adjust to, a user's emotional state or tailor their interactions with a user depending upon the user's emotional state. Even though a user may be in a certain emotional state when using the interactive software system or may have certain responses to the interactive software system that change his or her emotional state, interactive software systems are developed in a way that specifically attempts to provide the most useful service to as many of their users as possible, i.e., in a static "one size fits all" approach. Indeed, traditional interactive software systems are, by design, fairly generic in nature and often lack the malleability to meet the specific needs of a given user, much less respond to variations in the emotional state of a given user. As a result, an interactive software system designed for a generic, hypothetical user may alienate a specific user, who generally has a temperament that differs from the temperament of the generic, hypothetical user and whose emotional state may vary from interaction to interaction.

The inability of traditional interactive software systems to meet the needs of specific users and/or adjust to a user's emotional state often results in user frustration, and ultimately, in lost customers. This is because, predictably, when users are alienated from or become frustrated with an interactive software system, they are far more likely to abandon the interactive software system, which results in lost business.

For example, traditional interactive software systems offering tax return preparation services often present a static, predetermined, and pre-packaged user experience to all users as part of the tax return preparation interview process. These user experiences are typically presented to every user with little or no customization; are typically generated in a static and generic manner; and are typically provided via a combination of user experience components, which include, but are not limited to, interface displays, images, background music, and assistance resources. This is largely because traditional interactive software systems provide user experiences by employing static sets of user experience components, which are typically hard-coded elements of the interactive software system and do not lend themselves to effective or efficient modification, or even re-combination.

Because traditional interactive software systems provide a static and generic user experience, they are incapable of adapting the user experience to the user's emotional state. As a result, the user experience and any analysis associated with the user experience is a largely inflexible component of a given version of an interactive software system. Consequently, the user experience of a traditional interactive software system can only be modified through a redeployment or patch of the interactive software system itself. Therefore, there is little or no opportunity for any analytics associated with the user experience to react to the user's emotional state.

For example, in traditional interactive software systems offering tax return preparation services, the user experience elements presented to a user are pre-determined based on a generic user model that is, in fact and by design, not accurately representative of any "real world" user. It is therefore not surprising that many users, if not all users, of traditional interactive software systems find the experience, at best, impersonal. Specifically, users of traditional tax preparation interactive software systems may find the interview experience unnecessarily frustrating and unpleasant. Clearly, this is not the type of impression that results in happy, loyal, repeat customers.

Even worse, in many cases, the inability of traditional interactive software systems to detect or react to a user's emotional state causes users to become frustrated with their user experience, the software system, and the provider of the software system. Many of these users and customers then simply abandon the process and interactive software system completely and may, therefore, never become paying or repeat customers. Furthermore, given the speed and reach of modern communications, any complaints voiced by a dissatisfied user may reach a myriad of other, potential users. Indeed, the number of people that can become the audience for a single complaint is overwhelming and the potential reach of complaints can create serious consequences. For example, after his guitar was broken during a United Airlines flight, musician Dave Carrol filmed a video called "United Breaks Guitars," which showcased a song he wrote and performed, and uploaded it to YouTube. As of March 2015, the video has been viewed over 14.5 million times. Thus, one dissatisfied customer can have a ripple effect of lost customers. Clearly, this is an undesirable result for both the potential user of the interactive software system and the provider of the interactive software system.

Given the consequences of dissatisfied customers, it is in the best interest of the provider of an interactive software system to provide a dynamic and customized user experience to its users. What is needed is a method and system for obtaining emotional state data associated with a specific software system user and then using that emotional state data to individualize the user experience provided to the specific user.

SUMMARY

Embodiments of the present disclosure address some of the long-standing shortcomings associated with traditional interactive software systems by monitoring a user's emotional state and obtaining emotional state data. In one embodiment, the resulting emotional state data is analyzed and used to dynamically modify the user's experience by selecting one or more user experience components based on the analysis of the user's emotional state data. In this way, different types of user experience components can be utilized, and/or combined, by a single interactive software system, or multiple interactive software systems, to provide the user with an individualized user experience that is adapted to the user's current emotional state.

In addition, embodiments of the disclosure use the emotional state data associated with a user to detect that the user is in or is entering an undesirable emotional state. For example, in one embodiment, emotional state data is used to detect whether the user is becoming frustrated or stressed. Then, in one embodiment, different types of user experience components can be utilized, and/or re-combined, to adjust the user experience to adapt to the user's new emotional state, prevent the user from entering an undesirable emotional state, and/or encourage the user to enter into a desirable emotional state. In this way, the disclosed embodiments can be used to prevent the user from becoming frustrated with the interactive software system and potentially abandoning the interactive software system.

In one embodiment, one or more user experience components are identified and user experience component data representing the one or more user experience components is generated and stored in one or more partitioned user experience data sections of a memory device and/or system. In one embodiment, user experience components include, but are not limited to, individualized user interview questions and question sequences; user interfaces; interface displays; sub-displays; images; side bar displays; pop-up displays; alarms; music; backgrounds; avatars; highlighting mechanisms; icons; assistance resources; user recommendations; support recommendations; supplemental actions and recommendations; and/or any other components that individually, or in combination, create a user experience, as discussed herein, and/or as known in the art at the time of filing, and/or as developed after the time of filing.

In one embodiment, the emotional state data to be obtained and analyzed is identified and defined. In various embodiments, the emotional state data to be obtained and analyzed may include, but is not limited to, data associated with the user's own characterization of his or her emotional state; historical user data; data associated with a segment of users having characteristics comparable to the user; data associated with the user's pulse; the user's heart rate; the user's blood pressure; the user's facial expression; whether the user's eyebrows are raised; the shape of the user's eyebrows; whether the skin below the user's brow is stretched; the presence of wrinkles on the user's forehead; the location of wrinkles on the user's forehead; the extent to which the user's eyelids are opened; the extent to which the user's upper eyelid is opened; the extent to which the user's lower eyelid is opened; whether lines show below the user's lower eyelid; the amount of the white of the user's eye showing; the extent to which the user's jaw is open; whether the user's teeth are parted; whether the user's mouth is parted; whether the user's upper lip is raised; whether the user's lower lip is raised; the shape of the user's mouth; whether the user's nose is wrinkled; whether the user's nostrils are dilated; whether the user's cheeks are raised; whether the user's lower jaw juts out; the user's voice; the volume and frequency of the user's voice; the speed with which the user is speaking; the cadence with which the user is speaking; the user's body temperature; whether the user is perspiring; the amount of perspiration present on the user's skin; the force with which the user touches hardware associated with the interactive software system; the speed with which the user touches hardware associated with the interactive software system; and/or various other emotional state data similar to the specific illustrative user data examples discussed herein, and/or known in the art at the time of filing, and/or as developed after the time of filing.

In one embodiment, the emotional state data includes the user's pulse and is obtained using a heart rate monitor operatively coupled to, and/or otherwise associated with, a computing system used to implement at least part of the interactive software system. In one embodiment, the emotional state data includes the user's blood pressure and is obtained using a blood pressure monitor operatively coupled to, and/or otherwise associated with, a computing system used to implement at least part of the interactive software system. In one embodiment, the emotional state data includes the user's facial expression and is obtained using facial expression recognition software and/or hardware operatively coupled to, and/or otherwise associated with, a computing system used to implement at least part of the interactive software system. In one embodiment, the emotional state data includes the user's voice and is obtained using speech recognition software operatively coupled to, and/or otherwise associated with, a computing system used to implement at least part of the interactive software system. In one embodiment, the emotional state data includes the user's body temperature and is obtained using a temperature sensor operatively coupled to, and/or otherwise associated with, a computing system used to implement at least part of the interactive software system. In one embodiment, the emotional state data includes data measuring the user's perspiration and is obtained using a perspiration sensor operatively coupled to, and/or otherwise associated with, a computing system used to implement at least part of the interactive software system. In one embodiment, the emotional state data includes the force with which the user interacts with hardware associated with the interactive software system and is obtained using a pressure sensor associated with a keyboard, and/or mouse, touch screen, and/or other user interface system operatively coupled to, and/or otherwise associated with, a computing system used to implement at least part of the interactive software system. In one embodiment, the emotional state data includes the speed with which the user interacts with hardware associated with the interactive software system and is obtained using a sensor associated with a keyboard and/or mouse, touch screen, and/or other user interface system operatively coupled to, and/or otherwise associated with, a computing system used to implement at least part of the interactive software system.

Numerous means, methods, systems, algorithms, procedures, and processes are known in the art for detecting emotional states, and/or obtaining emotional state data associated with a user. Consequently, a more detailed discussion of any particular means, method, system, algorithm, procedure, and process for detecting emotional states, and/or obtaining emotional state data, associated with a user is omitted here to avoid detracting from the invention.

In one embodiment, emotional state threshold parameter data associated with each type of emotional state data is identified and defined. In one embodiment, a specific emotional state threshold parameter data is defined for each type of emotional state data to establish whether a user has reached, or is approaching, an associated emotional state.

For example, a defined emotional state threshold parameter may provide that when a user's heart is beating a rate greater than 100 beats per minute, the user is in, or is approaching, a stressed emotional state.

In one embodiment, the emotional state threshold parameter data associated with one or more of the one or more types of emotional state data is identified and defined based on emotional state data obtained from a group of people, and/or norms obtained from various medical data processors and medical institutions. In one embodiment, the emotional state threshold parameter data associated with one or more of the one or more types of emotional state data is identified and defined based on emotional state data obtained from the specific user, i.e. the emotional state threshold parameter data is customized to the specific, current user. In some of these embodiments, the emotional state threshold parameter data associated with one of the one or more types of emotional state data from a group of people and/or norms obtained from various medical data processors and medical institutions is initially used as base data and then a customized emotional profile for the specific user is developed based on feedback from the specific user and emotional data monitoring of the specific user.

According to one embodiment, as a user is interacting with the interactive software system, the emotional state data associated with the user is monitored and/or obtained using one or more processes, systems, mechanisms or means for obtaining emotional state data, as discussed herein, and/or as known in the art at the time of filing, and/or as developed after the time of filing. In one embodiment, the emotional state data associated with the user is provided to one or more analytics modules. In one embodiment, under the direction of the one or more analytics modules, the emotional state data associated with the user is analyzed and/or compared to the emotional state threshold parameter data associated with the type of emotional state data received.

In one embodiment, the one or more analytics modules are "pluggable," e.g., interchangeable, analytics modules/components to be used with one or more interactive software systems that can be selected, interfaced with, and interchanged, without requiring the redeployment of either the interactive software system or any individual analytics module. In this way, different types of emotional state data can be analyzed and utilized by a single interactive software system or version, or interactive software systems and/or versions, and different analytic algorithms can be interchangeably deployed. As a result, individualized user experiences can be provided that are composed of different user experience components, including, but not limited to, individualized user interview questions and question sequences; user interfaces; interface displays; sub-displays; images; side bar displays; pop-up displays; alarms; music; backgrounds; avatars; highlighting mechanisms; icons; assistance resources; user recommendations; supplemental actions and recommendations; and/or any other components that individually, or in combination, create a user experience, as discussed herein, and/or as known in the art at the time of filing, and/or as developed after the time of filing.

In one embodiment, based on the analysis of the emotional state data associated with the user, a current emotional state of the user is determined. In one embodiment, based at least in part on the determined current emotional state of the user, the interactive software system adapts to provide an individualized user experience to the user by presenting a set of the user experience components to the user that is customized based on the user's emotional state data and the analysis of one or more analytics algorithms provided through the one or more interchangeable analytics modules.

For example, if the user's emotional state data shows that the user's heart is beating at a rate of 110 beats per minute and the defined emotional state threshold parameter data provides that when a user's heart is beating a rate greater than 100 beats per minute the user is in a stressed emotional state, the emotional state data and the emotional state threshold parameter data is analyzed by the one or more analytics algorithms provided through the one or more interchangeable analytics modules and a determination is made that the user is in the stressed emotional state. Consequently, in this specific illustrative example, a user experience component or combination of user experience components are selected by one of the one or more analytics modules to create a user experience with a stress-reducing effect.

For example, in one embodiment, if a user is in a stressed emotional state, a user experience component or combination of user experience components may be selected to provide the user with soothing background colors as part of the user experience. In one embodiment, if the user is in a stressed emotional state, a user experience component or combination of user experience components may be selected to provide the user with soft music as part of the user experience. In one embodiment, if a user is in a stressed emotional state, a user experience component or combination of user experience components may be selected to provide the user with additional assistance as part of the user experience.

As noted above, in one embodiment, user experience components are determined by the one or more analytics modules described herein based on emotional state data such as, but not limited to, the user's own characterization of his or her emotional state, historical user data, data associated with a segment of users having characteristics comparable to the user; the user's heart rate, the user's blood pressure, the volume of the user's voice, the speed with which the user is speaking, the cadence with which the user is speaking, the user's body temperature, whether the user is perspiring, the amount of perspiration present on the user's skin, the force with which the user interacts with hardware associated with the interactive software system, the speed with which the user interacts with hardware associated with the interactive software system, and/or various other emotional state data similar to the specific illustrative user data examples discussed herein.

According to one embodiment, other user experience components such as, but not limited to, individualized user interview questions and question sequences, user interfaces, interface displays, sub-displays, images, side bar displays, pop-up displays, alarms, music, backgrounds, avatars, highlighting mechanisms, icons, assistance resources, user recommendations, supplemental actions and recommendations, and/or any other components that individually, or in combination, create a user experience, as discussed herein, and/or as known in the art at the time of filing, and/or as developed after the time of filing, are adapted, adjusted, ordered, and/or otherwise customized to the current user, based on the user's current emotional state as determined by relatively real-time analysis of the user's emotional state data by the one or more of the interchangeable analytics modules described herein.

In one embodiment, by customizing the user experience based on the emotional state data and analysis described herein, the user experience associated with the interactive software system can be improved and customized to a selected user's emotional state at the time the user is interacting with the interactive software system. According to one embodiment, by improving the user experience using the emotional state data, the interactive software system user experience is personal to the user and dynamically adapted to the user's current emotional state. Thus, using the disclosed method and system for using emotional state data to tailor the user experience of an interactive software system results in more efficient use of resources by reducing the number of instances where data is entered by a user and processed by the interactive system only for the user to abandon the interactive software system. Consequently, using the disclosed method and system for using emotional state data to tailor the user experience of an interactive software system results in the use of fewer processing cycles, reduced and more efficient use of memory, and reduced use of communications bandwidth to relay data. As a result computing systems and networks implementing the disclosed method and system for using emotional state data to tailor the user experience of an interactive software system are faster, more efficient, and more effective.

According to one embodiment, after the user experience is individualized and as a user is interacting with the interactive software system, the emotional state data associated with that user is monitored and/or obtained on a periodic or ongoing basis using one or more processes, systems, mechanisms, and/or means for obtaining emotional state data, as discussed herein, and/or as known in the art at the time of filing, and/or as developed after the time of filing. In one embodiment, the emotional state data associated with the user is provided to one or more analytics modules. In one embodiment, under the direction of the one or more analytics modules, the emotional state data associated with the user is analyzed and/or compared to the emotional state threshold parameter data associated with the type of emotional state data received. In one embodiment, as the emotional state data associated with the user changes, the user experience is re-adapted to the users changing emotional state by recombining the user experience components dynamically, and in relative real-time.

As noted above, in one embodiment, individualizing the user experience within the interactive software system is accomplished, at least in part, by providing the emotional state data associated with a selected user to one or more of the selected interchangeable analytics modules described herein. In one embodiment, the selected interchangeable analytics modules then process the user data according to the specific one or more analytics algorithms included in the selected interchangeable analytics modules to generate, specify, and/or determine which user experience components are to be provided to the user. According to one embodiment, instead of modifying the entire interactive software system, improvements to analytics algorithms for individualizing user experience components may be updated simply by replacing or overwriting a prior version of the selected one or more interchangeable analytics modules with an updated version of the selected one or more interchangeable analytics modules, potentially saving significant time and development costs, by providing a "plug and play," real-time/minimal down time modification capability.

Therefore, the various embodiments of the disclosure, and their associated benefits, as discussed herein, improve the technical field of interactive software systems and data processing by using emotional state data to dynamically individualize the user experience provided through the interactive software system in an evolving, dynamic, manner that is not only customized to an individual user, but also to the varying emotional states of a specific individual user. Consequently, the disclosed embodiments amount to significantly more than an implementation of the abstract idea of customizing a user experience to a specific user.

Figure 1:
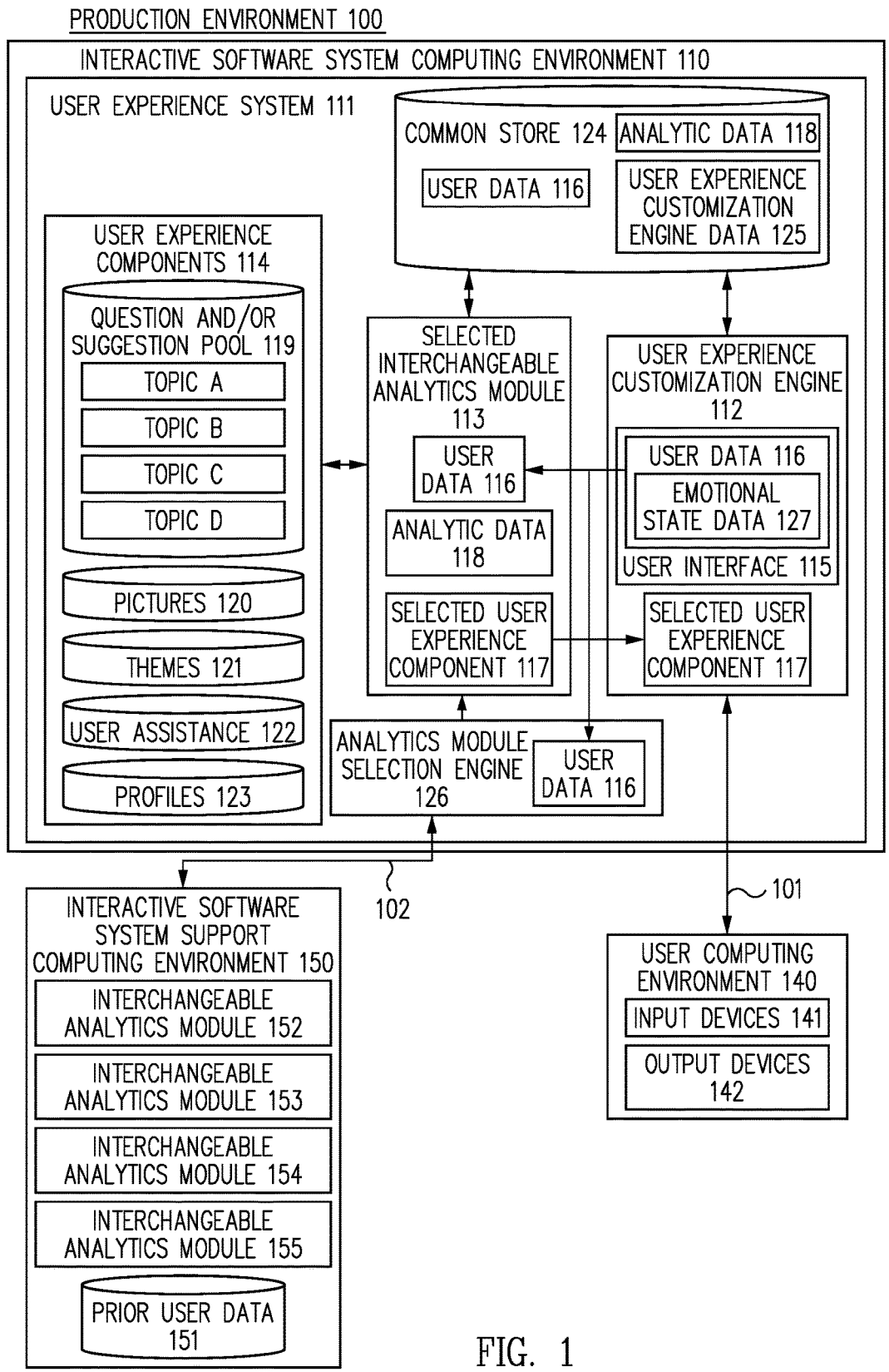
FIG. 1 is a block diagram of software architecture for providing an interactive software system with a user experience adapted to a user's emotional state, in accordance with one embodiment.

Common reference numerals are used throughout the FIG.s and the detailed description to indicate like elements. One skilled in the art will readily recognize that the above FIG.s are examples and that other architectures, modes of operation, orders of operation, and elements/functions can be provided and implemented without departing from the characteristics and features of the invention, as set forth in the claims.

DETAILED DESCRIPTION

Embodiments will now be discussed with reference to the accompanying FIG.s, which depict one or more exemplary embodiments. Embodiments may be implemented in many different forms and should not be construed as limited to the embodiments set forth herein, shown in the FIG.s, and/or described below. Instead, these exemplary embodiments are provided to allow a complete disclosure that conveys the principles of the invention, as set forth in the claims, to those of skill in the art.

The INTRODUCTORY SYSTEM, HARDWARE ARCHITECTURE, and PROCESS sections herein describe systems and processes suitable for using emotional state data to tailor the user experience of an interactive software system.

Introductory System

Herein, the term "interactive software system" can be, but is not limited to, any data management system implemented on a computing system, accessed through one or more servers, accessed through a network, accessed through a cloud, and/or provided through any system or by any means, as discussed herein, and/or as known in the art at the time of filing, and/or as developed after the time of filing, that gathers/obtains data from one or more sources, provides data to one or more sources, and/or has the capability to analyze at least part of the data.

The term "interactive software system" includes, but is not limited to, any software system that provides an interactive user experience to its users and is implemented on a computing system, accessed through one or more servers, accessed through a network, accessed through a cloud, and/or provided through any computing system or by any means as discussed herein, as known in the art at the time of filing, and/or as developed after the time of filing.

As used herein, the term "interactive software system" includes, but is not limited to, the following: web-based, online, and/or computing system implemented personal and/or business tax preparation systems, services, packages, programs, modules, or applications; web-based, online, and/ or computing system implemented personal and/or business financial management systems, services, packages, programs, modules, or applications; web-based, online, and/or computing system implemented personal and/or business management systems, services, packages, programs, modules, or applications; web-based, online, and/or computing system implemented personal and/or business accounting and/or invoicing systems, services, packages, programs, modules, or applications; and various other personal and/or business electronic data management systems, services, packages, programs, modules, or applications, whether known at the time of filing or as developed later.

Specific examples of interactive software systems include, but are not limited to the following: TurboTax™ available from Intuit, Inc. of Mountain View, Calif.; TurboTax Online™ available from Intuit, Inc. of Mountain View, Calif.; Quicken™, available from Intuit, Inc. of Mountain View, Calif.; Quicken Online™, available from Intuit, Inc. of Mountain View, Calif.; QuickBooks™, available from Intuit, Inc. of Mountain View, Calif.; QuickBooks Online™, available from Intuit, Inc. of Mountain View, Calif.; Mint™, available from Intuit, Inc. of Mountain View, Calif.; Mint Online™, available from Intuit, Inc. of Mountain View, Calif.; and/or various other software systems discussed herein, and/or known to those of skill in the art at the time of filing, and/or as developed after the time of filing.

As used herein, the terms "computing system," "computing device," and "computing entity," include, but are not limited to, the following: a server computing system; a workstation; a desktop computing system; a mobile computing system, including, but not limited to, smart phones, portable devices, and/or devices worn or carried by a user; a database system or storage cluster; a virtual asset; a switching system; a router; any hardware system; any communications system; any form of proxy system; a gateway system; a firewall system; a load balancing system; or any device, subsystem, or mechanism that includes components that can execute all, or part, of any one of the processes and/or operations as described herein.

In addition, as used herein, the terms "computing system," "computing device," and "computing entity," can denote, but are not limited to the following: systems made up of multiple virtual assets, server computing systems, workstations, desktop computing systems, mobile computing systems, database systems or storage clusters, switching systems, routers, hardware systems, communications systems, proxy systems, gateway systems, firewall systems, load balancing systems, or any devices that can be used to perform the processes and/or operations as described herein.

Herein, the terms "mobile computing system" and "mobile device" are used interchangeably and include, but are not limited to the following: a smart phone; a cellular phone; a digital wireless telephone; a tablet computing system; a notebook computing system; any portable computing system; a two-way pager; a Personal Digital Assistant (PDA); a media player; an Internet appliance; or any other movable/mobile device and/or computing system that includes components that can execute all, or part, of any one of the processes and/or operations as described herein.

Herein, the terms "mobile computing system" and "mobile device" specifically include devices worn or carried by a user such as, but not limited to, smart watches, wearable Personal Digital Assistants (PDAs); wearable media players; wearable Internet appliances; wearable phones; and/or any other computing system that can be worn by a user and that includes components that can execute all, or part, of any one of the processes and/or operations as described herein.

Herein, the term "production environment" includes the various components, or assets, used to deploy, implement, access, and use, a given software system as that software system is intended to be used. In various embodiments, production environments include multiple computing systems and/or assets that are combined, communicatively coupled, virtually and/or physically connected, and/or associated with one another, to provide the production environment implementing the application.

As specific illustrative examples, the assets making up a given production environment can include, but are not limited to, the following: one or more computing environments used to implement at least part of the software system in the production environment such as a data center, a cloud computing environment, a dedicated hosting environment, and/or one or more other computing environments in which one or more assets used by the application in the production environment are implemented; one or more computing systems or computing entities used to implement at least part of the software system in the production environment; one or more virtual assets used to implement at least part of the software system in the production environment; one or more supervisory or control systems, such as hypervisors, or other monitoring and management systems used to monitor and control assets and/or components of the production environment; one or more communications channels for sending and receiving data used to implement at least part of the software system in the production environment; one or more access control systems for limiting access to various components of the production environment, such as firewalls and gateways; one or more traffic and/or routing systems used to direct, control, and/or buffer data traffic to components of the production environment, such as routers and switches; one or more communications endpoint proxy systems used to buffer, process, and/or direct data traffic, such as load balancers or buffers; one or more secure communication protocols and/or endpoints used to encrypt/decrypt data, such as Secure Sockets Layer (SSL) protocols, used to implement at least part of the software system in the production environment; one or more databases used to store data in the production environment; one or more internal or external services used to implement at least part of the software system in the production environment; one or more backend systems, such as backend servers or other hardware used to process data and implement at least part of the software system in the production environment; one or more software modules/functions used to implement at least part of the software system in the production environment; and/or any other assets/components making up an actual production environment in which at least part of the software system is deployed, implemented, accessed, and run, e.g., operated, as discussed herein, and/or as known in the art at the time of filing, and/or as developed after the time of filing.

As used herein, the term "computing environment" includes, but is not limited to, a logical or physical grouping of connected or networked computing systems and/or virtual assets using the same infrastructure and systems such as, but not limited to, hardware systems, software systems, and networking/communications systems. Typically, computing environments are either known, "trusted" environments or unknown, "untrusted" environments. Typically, trusted computing environments are those where the assets, infrastructure, communication and networking systems, and security systems associated with the computing systems and/or virtual assets making up the trusted computing environment, are either under the control of, or known to, a party.

In various embodiments, each computing environment includes allocated assets and virtual assets associated with, and controlled or used to create, and/or deploy, and/or operate at least part of the software system.

In various embodiments, one or more cloud computing environments are used to create, and/or deploy, and/or operate at least part of the software system that can be any form of cloud computing environment, such as, but not limited to, a public cloud; a private cloud; a virtual private network (VPN); a subnet; a Virtual Private Cloud (VPC); a sub-net or any security/communications grouping; or any other cloud-based infrastructure, sub-structure, or architecture, as discussed herein, and/or as known in the art at the time of filing, and/or as developed after the time of filing.

In many cases, a given software system or service may utilize, and interface with, multiple cloud computing environments, such as multiple VPCs, in the course of being created, and/or deployed, and/or operated.

As used herein, the term "virtual asset" includes any virtualized entity or resource, and/or virtualized part of an actual, or "bare metal" entity. In various embodiments, the virtual assets can be, but are not limited to, the following: virtual machines, virtual servers, and instances implemented in a cloud computing environment; databases associated with a cloud computing environment, and/or implemented in a cloud computing environment; services associated with, and/or delivered through, a cloud computing environment; communications systems used with, part of, or provided through a cloud computing environment; and/or any other virtualized assets and/or sub-systems of "bare metal" physical devices such as mobile devices, remote sensors, laptops, desktops, point-of-sale devices, etc., located within a data center, within a cloud computing environment, and/or any other physical or logical location, as discussed herein, and/or as known/available in the art at the time of filing, and/or as developed/made available after the time of filing.

In various embodiments, any, or all, of the assets making up a given production environment discussed herein, and/or as known in the art at the time of filing, and/or as developed after the time of filing can be implemented as one or more virtual assets.

In one embodiment, two or more assets, such as computing systems and/or virtual assets, and/or two or more computing environments are connected by one or more communications channels including but not limited to, Secure Sockets Layer (SSL) communications channels and various other secure communications channels, and/or distributed computing system networks, such as, but not limited to the following: a public cloud; a private cloud; a virtual private network (VPN); a subnet; any general network, communications network, or general network/communications network system; a combination of different network types; a public network; a private network; a satellite network; a cable network; or any other network capable of allowing communication between two or more assets, computing systems, and/or virtual assets, as discussed herein, and/or available or known at the time of filing, and/or as developed after the time of filing.

As used herein, the term "network" includes, but is not limited to, any network or network system such as, but not limited to, the following: a peer-to-peer network; a hybrid peer-to-peer network; a Local Area Network (LAN); a Wide Area Network (WAN); a public network, such as the Internet; a private network; a cellular network; any general network, communications network, or general network/communications network system; a wireless network; a wired network; a wireless and wired combination network; a satellite network; a cable network; any combination of different network types; or any other system capable of allowing communication between two or more assets, virtual assets, and/or computing systems, whether available or known at the time of filing or as later developed.

Herein, the term "emotional state" refers to an emotional state of a user and includes, but is not limited to, a happy emotional state or happiness; a sad emotional state or sadness; a surprised emotional state or surprise; a fearful emotional state or fear; a disgusted emotional state or disgust; an angry emotional state or anger; a tense emotional state; a nervous emotional state; a stressed emotional state; an upset emotional state; a frustrated emotional state; a depressed emotional state; a bored emotional state; a fatigued emotional state; an alert emotional state; an excited emotional state; an elated emotional state; a contented emotional state; a serene emotional state; a relaxed emotional state; and/or a calm emotional state.

As used herein, the term "emotional state data" refers to a quantitative representation of a predicted emotional state and/or combination of emotional states and/or physiological, behavioral, and/or experiential indications of an emotional state and/or a combination of emotional states.

As used herein, the term "emotional state threshold parameter" refers to specific values and/or ranges of values associated with a particular emotional state or combination of emotional states.

Herein, the term "user experience" includes the practical, experiential, affective, significant, and/or valuable aspects of human—software interaction including, but not limited to, data entry, question submission, and/or interview process. As used herein, the term "user experience" includes not only the data entry, question submission, and/or interview process, but also other user experience components provided or displayed to the user such as, but not limited to, the following: individualized user interview questions and question sequences, user interfaces, interface displays, sub-displays, images, side bar displays, pop-up displays, alarms, music, backgrounds, avatars, highlighting mechanisms, icons, assistance resources, user recommendations, supplemental actions and recommendations, and/or any other components that individually, or in combination, create a user experience, as discussed herein, and/or as known in the art at the time of filing, and/or as developed after the time of filing.

Herein, the term "party," "user," "user consumer," and "customer" are used interchangeably to denote any party and/or entity that interfaces with, and/or to whom information is provided by, the method and system for using emotional state data to tailor the user experience of an interactive software system described herein, and/or a person and/or entity that interfaces with, and/or to whom information is provided by, the method and system for using emotional state data to tailor the user experience of an interactive software system described herein, and/or a legal guardian of person and/or entity that interfaces with, and/or to whom information is provided by, the method and system for using emotional state data to tailor the user experience of an interactive software system described herein, and/or an authorized agent of any party and/or person and/or entity that interfaces with, and/or to whom information is provided by, the method and system for using emotional state data to tailor the user experience of an interactive software system described herein. For instance, in various embodiments, a user can be, but is not limited to, a person, a commercial entity, an application, a service, and/or a computing system.

Hardware Architecture

FIG. 1 illustrates a block diagram of a PRODUCTION ENVIRONMENT 100 for providing an interactive software system with a user experience adapted to a user's emotional state, according to one embodiment. According to one embodiment, PRODUCTION ENVIRONMENT 100 provides an interactive software system with a user experience adapted to a user's emotional state by monitoring and obtaining data about a user's emotional state, analyzing the resulting emotional state data, selecting a user experience component based on the analysis of the user's emotional state data, and presenting the selected user experience component to the user.

As discussed above, there are various long-standing shortcomings associated with traditional interactive software systems. Because traditional interactive software systems present a static user experience to their users without consideration of an individual user's mood or personal situation, the individual user is provided with a static user experience incapable of dynamically meeting his or her needs. Because of this static user experience, traditional interactive software systems provide a user experience that is impersonal and has historically been a source of confusion and frustration to a user. Using traditional interactive software systems, users who are confused, frustrated, and even alienated by an irrelevant or inappropriate user experience, often fail to obtain the maximum benefit offered by the interactive software system or even abandon the interactive software system altogether. As a result, traditional interactive software systems may fail to generate an optimum benefit to the user, e.g., the benefit the user would be provided if the user were provided a dynamically responsive user experience.

For example, a user who is calm and content may begin interacting with a financial planning service associated with an interactive software system to provide information to the financial planning service for the purpose of determining a retirement savings strategy. As the process of providing information goes on, the user may begin to realize that she will have to work for more years than she had planned in order to save a sufficient amount of money to retire. Understandably, the user may become frustrated and stressed. By providing a user experience that monitors, predicts, and/or responds to the user's changing emotional state, the interactive software system can manage the user's emotional state and provide better service to the user. As a result of this better service, the user may continue working with the interactive software system and ultimately exit the system in a calmer emotional state than if the user had been left to deal with a static, generic user experience.

Inefficiencies associated with updating traditional interactive software systems are an additional long-standing shortcoming. Even if potential improvements to traditional interactive software systems become available, the costs associated with developing, testing, releasing, and debugging a new version of the interactive software system each time a new or improved analytic algorithm is discovered, or defined, will often outweigh the benefits gained by a user, or even a significant sub-set of users.

PRODUCTION ENVIRONMENT 100 is utilized to implement one illustrative embodiment of a system for providing an interactive software system with a user experience adapted to a user's emotional state which addresses some of the shortcomings associated with traditional interactive software systems by dynamically selecting user experience components to customize the user experience presented to an individual user. Which user experience components or combination of user experience components are selected depends upon user data, including emotional state data associated with a user, according to one embodiment. As a result, embodiments of the present disclosure improve the technical fields of user experience, customer service, and data flow and distribution by enabling an interactive software system to provide a more thorough and customized user experience to the user.

In addition, by minimizing, or potentially eliminating, the processing and presentation of irrelevant user experience components, implementation of embodiments of the present disclosure allows for significant improvement to the field of data collection and data processing. As one illustrative example, by minimizing, or potentially eliminating, the processing and presentation of irrelevant question and/or suggestion data to a user, implementation of embodiments of the present disclosure allows for relevant data collection using fewer processing cycles and less communications bandwidth. As a result, embodiments of the present disclosure allow for improved processor performance, more efficient use of memory access and data storage capabilities, reduced communication channel bandwidth utilization, and faster communications connections. Consequently, computing and communication systems implementing and/or providing the embodiments of the present disclosure are transformed into faster and more operationally efficient devices and systems.

According to one embodiment, PRODUCTION ENVIRONMENT 100 includes INTERACTIVE SOFTWARE SYSTEM COMPUTING ENVIRONMENT 110, USER COMPUTING ENVIRONMENT 140, and INTERACTIVE SOFTWARE SYSTEM SUPPORT COMPUTING ENVIRONMENT 150 for customizing a user experience for a user, according to one embodiment. Computing environments 110, 140, and 150 are communicatively coupled to each other with communication channel 101 and communication channel 102.

In one embodiment communication channels 101 and 102 are any communications channels as discussed herein, as known in the art at the time of filing, and/or as known in the art after the time of filing. Those of skill in the art will readily recognize that in various embodiments, communication channels 101 and 102 can be the same communications channel or implemented across two or more communications channels.

According to one embodiment, INTERACTIVE SOFTWARE SYSTEM COMPUTING ENVIRONMENT 110 represents one or more computing systems such as, but not limited to, a server, a computing cabinet, and/or distribution center that is configured to receive, execute, and host one or more user experience applications for access by one or more users. In one embodiment, INTERACTIVE SOFTWARE SYSTEM COMPUTING ENVIRONMENT 110 includes USER EXPERIENCE SYSTEM 111 for individualizing a user experience, according to one embodiment. USER EXPERIENCE SYSTEM 111 includes various components, databases, engines, modules, and data to facilitate the customization of a user experience. In one embodiment, USER EXPERIENCE SYSTEM 111 includes USER EXPERIENCE CUSTOMIZATION ENGINE 112, SELECTED INTERCHANGEABLE ANALYTICS MODULE 113, and USER EXPERIENCE COMPONENTS 114.

In various embodiments, SELECTED INTERCHANGEABLE ANALYTICS MODULE 113 is an interchangeable or pluggable component within PRODUCTION ENVIRONMENT 100 and enables PRODUCTION ENVIRONMENT 100 to provide an interactive software system with a user experience adapted to a user's emotional state with different algorithms or analysis routines by overwriting/replacing one interchangeable analytics module with another, according to one embodiment. The function and plug-ability of the interchangeable analytics module enables PRODUCTION ENVIRONMENT 100 to provide an interactive software system with a user experience adapted to a user's emotional state with a customized user experience and to update the individualization algorithms without altering other parts of PRODUCTION ENVIRONMENT 100, i.e., the interactive software system itself, according to one embodiment.

In one embodiment, USER EXPERIENCE CUSTOMIZATION ENGINE 112 provides the user with a user experience by receiving USER DATA 116 and by presenting the user with SELECTED USER EXPERIENCE COMPONENT 117, such as, but not limited to, data entry; question and/or suggestion submission; interview process; individualized user interview questions and/or suggestions and question and/or suggestion sequences; user interfaces; interface displays; sub-displays; images; side bar displays; pop-up displays; alarms; music; backgrounds; avatars; highlighting mechanisms; icons; assistance resources; user recommendations; supplemental actions and recommendations; and/or any other components that individually, or in combination, create a user experience, as discussed herein, and/or as known in the art at the time of filing, and/or as developed after the time of filing.

According to one embodiment, USER EXPERIENCE CUSTOMIZATION ENGINE 112 includes USER INTERFACE 115 to receive USER DATA 116 and to present the user with SELECTED USER EXPERIENCE COMPONENT 117, according to one embodiment. USER EXPERIENCE CUSTOMIZATION ENGINE 112 employs USER INTERFACE 115 to receive USER DATA 116 from INPUT DEVICES 141 of USER COMPUTING ENVIRONMENT 140 and employs USER INTERFACE 115 to transmit SELECTED USER EXPERIENCE COMPONENT 117 to OUTPUT DEVICES 142 of USER COMPUTING ENVIRONMENT 140.

In one embodiment, USER DATA 116 includes EMOTIONAL STATE DATA 127. In various embodiments, EMOTIONAL STATE DATA 127 is data representing one or more emotional states, including, but not limited to, the following: a tense emotional state; a nervous emotional state; a stressed emotional state; an upset emotional state; a frustrated emotional state; a sad emotional state; a depressed emotional state; a bored emotional state; a fatigued emotional state; an alert emotional state; an excited emotional state; an elated emotional state; a happy emotional state; a contented emotional state; a serene emotional state; a relaxed emotional state; and/or a calm emotional state. In various embodiments, EMOTIONAL STATE DATA 127 represents more than one emotional state.

In various embodiments, EMOTIONAL STATE DATA 127 may include, but is not limited to, data associated with the user's own characterization of his or her emotional state; historical user data; a segment of users having characteristics comparable to the user; the user's pulse; the user's heart rate; the user's blood pressure; the user's facial expression; the user's voice; the volume and frequency of the user's voice; the speed with which the user is speaking; the cadence with which the user is speaking; the user's body temperature; whether the user is perspiring; the amount of perspiration present on the user's skin; the force with which the user touches hardware associated with the interactive software system; the speed with which the user touches hardware associated with the interactive software system; and/or various other emotional state data similar to the specific illustrative user data examples discussed herein known in the art at the time of filing, and/or as developed after the time of filing.

In various embodiments, EMOTIONAL STATE DATA 127 can include, but is not limited to, data acquired from the user's characterization of his or her emotional state; data acquired from historical user data; data acquired from a segment of users having characteristics comparable to the user; data acquired from measuring the user's heart beat; data acquired from measuring the user's eye rotation; data acquired from measuring the user's perspiration; data acquired from measuring the user's respiration; data acquired from measuring the user's oxygen saturation; data acquired from measuring the user's blood pressure; data acquired from measuring the user's skin temperature; data acquired from measuring the user's muscle tension; data acquired from measuring the user's neural activity; data acquired from measuring the user's eye blinking; data acquired from measuring the user's facial expression; data acquired from measuring the user's voice and/or speech; and/or data acquired from measuring the user's interactions with hardware associated with an interactive software system.

According to various embodiments, SELECTED USER EXPERIENCE COMPONENT 117 is received from SELECTED INTERCHANGEABLE ANALYTICS MODULE 113 after SELECTED INTERCHANGEABLE ANALYTICS MODULE 113 analyzes USER DATA 116. SELECTED USER EXPERIENCE COMPONENT 117 can include, but is not limited to, data representing individualized user interview questions and/or suggestions and question and/or suggestion sequences; user interfaces; interface displays; sub-displays; images; music; backgrounds; avatars; highlighting mechanisms; icons; assistance resources; user recommendations; supplemental actions and recommendations; and/or any other component that individually, or in combination, create a user experience, as discussed herein, and/or as known in the art at the time of filing, and/or as developed after the time of filing, that are displayed in, or as part of, the USER INTERFACE 115.

According to one embodiment, SELECTED INTERCHANGEABLE ANALYTICS MODULE 113 receives USER DATA 116 from USER EXPERIENCE CUSTOMIZATION ENGINE 112, analyzes USER DATA 116, and selects SELECTED USER EXPERIENCE COMPONENT 117 based on USER DATA 116. In one embodiment, SELECTED INTERCHANGEABLE ANALYTICS MODULE 113 is an interchangeable module within USER EXPERIENCE SYSTEM 111. In other words, in one embodiment, SELECTED INTERCHANGEABLE ANALYTICS MODULE 113 can be modified, overwritten, deleted, replaced, and/or updated with different and/or improved analytics modules, such as any of INTERCHANGEABLE ANALYTICS MODULES 152, 153, 154, and 155, of INTERACTIVE SOFTWARE SYSTEM SUPPORT COMPUTING ENVIRONMENT 150, without requiring modification to other components within USER EXPERIENCE SYSTEM 111, according to one embodiment. An advantage of implementing SELECTED INTERCHANGEABLE ANALYTICS MODULE 113 as an interchangeable module is that, while one version of SELECTED INTERCHANGEABLE ANALYTICS MODULE 113 is being executed, other analytics modules, such as INTERCHANGEABLE ANALYTICS MODULES 152, 153, 154, and 155, of INTERACTIVE SOFTWARE SYSTEM SUPPORT COMPUTING ENVIRONMENT 150, can be developed and tested. One or more of INTERCHANGEABLE ANALYTICS MODULES 152, 153, 154, and 155 can then be made available to USER EXPERIENCE CUSTOMIZATION ENGINE 112 without making changes to USER EXPERIENCE CUSTOMIZATION ENGINE 112, or other components within USER EXPERIENCE SYSTEM 111.

According to one embodiment, SELECTED INTERCHANGEABLE ANALYTICS MODULE 113 is configured to receive and respond to commands, requests, instructions, and/or other communications from USER EXPERIENCE CUSTOMIZATION ENGINE 112 using an application programming interface ("API"). For example, SELECTED INTERCHANGEABLE ANALYTICS MODULE 113 receives USER DATA 116 from USER EXPERIENCE CUSTOMIZATION ENGINE 112 through one or more API-based requests or commands from USER EXPERIENCE CUSTOMIZATION ENGINE 112, according to one embodiment. As another example, SELECTED INTERCHANGEABLE ANALYTICS MODULE 113 transmits SELECTED USER EXPERIENCE COMPONENT 117 to USER EXPERIENCE CUSTOMIZATION ENGINE 112 using one or more API-based functions, routines, and/or calls, according to one embodiment.

According to one embodiment, SELECTED INTERCHANGEABLE ANALYTICS MODULE 113 draws from USER EXPERIENCE COMPONENTS 114 to select SELECTED USER EXPERIENCE COMPONENT 117. In one embodiment, SELECTED INTERCHANGEABLE ANALYTICS MODULE 113 draws from USER EXPERIENCE COMPONENTS 114 to select a combination of more than one SELECTED USER EXPERIENCE COMPONENT 117. According to one embodiment, SELECTED INTERCHANGEABLE ANALYTICS MODULE 113 can apply any one of a number of algorithms or analysis techniques to USER DATA 116 to generate ANALYTIC DATA 118. In one embodiment, ANALYTIC DATA 118 can represent the application of a predictive model, a collaborative filter, or other analytics to USER DATA 116. In one embodiment, ANALYTIC DATA 118 represents the application of emotional state threshold parameter data to EMOTIONAL STATE DATA 127.

In one embodiment, SELECTED INTERCHANGEABLE ANALYTICS MODULE 113 determines, chooses, and/or individualizes the user's user experience by selecting one or more SELECTED USER EXPERIENCE COMPONENT 117 from USER EXPERIENCE COMPONENTS 114, based at least partially on ANALYTIC DATA 118 and/or USER DATA 116.

In one embodiment, USER EXPERIENCE COMPONENTS 114 include, but are not limited to, QUESTION AND/OR SUGGESTION POOL 119, PICTURES 120, THEMES 121, USER ASSISTANCE 122, and PROFILES 123. In one embodiment, QUESTION AND/OR SUGGESTION POOL 119 includes all of the questions and/or suggestions that can and/or must be presented and/or made available to a user during the user's interaction with the interactive software system. In one embodiment, QUESTION AND/OR SUGGESTION POOL 119 groups the questions and/or suggestions by topic. In the specific illustrative example of FIG. 1, QUESTION AND/OR SUGGESTION POOL 119 includes four groups of questions and/or suggestions that are represented by topic A, topic B, topic C, and topic D, according to one embodiment. While QUESTION AND/OR SUGGESTION POOL 119 is represented as having four topics, it is to be understood that the questions and/or suggestions can be categorized into many more or less topics, according to various embodiments.

As a specific illustrative example, in an interactive software system that provides a tax preparation service, examples of topics by which QUESTION AND/OR SUGGESTION POOL 119 may be grouped in one embodiment include, but are not limited to, one or more of: earned income credit, child tax credit, charitable contributions, cars and personal property, education, medical expenses, taxes paid, moving expenses, job expenses, residential energy credits, property taxes, mortgage interest, interest and dividend income, and the like. In addition, in this specific illustrative example, QUESTION AND/OR SUGGESTION POOL 119 is grouped by high-level topics such as home, self and family; charitable contributions; education; medical; and the like. In addition, in this specific illustrative example, QUESTION AND/OR SUGGESTION POOL 119 includes low-level topics that are subgroups of the high-level topics, and include, but are not limited to, mortgage interest credit; homebuyer credit; elderly/disabled credit; legal fees; student loan interest; scholarships; state and local tax refunds; and/or any other form of question and/or suggestion and/or data acquisition, as discussed herein, and/or as known in the art at the time of filing, and/or as developed after the time of filing.

In one embodiment, PICTURES 120 and THEMES 121 include variations for USER EXPERIENCE COMPONENTS 114 that can be used by USER EXPERIENCE CUSTOMIZATION ENGINE 112 to provide an individualized user experience to a user. In one embodiment, PICTURES 120 include images of varying topics/themes, shapes, sizes, and colors that can be used as part of the user experience while communicating with the user. In one embodiment, PICTURES 120 can be positioned proximate to questions and/or suggestions or question and/or suggestion topics to assist the user in understanding the gist of the series of questions and/or suggestions being presented, according to one embodiment. For example, PICTURES 120 can include a house, a doctor or stethoscope, children, a school, a car, and the like, according to one embodiment. In one embodiment, THEMES 121 include background colors, font colors, font sizes, animations, avatars, other theme-related graphics, background music, etc., which can be used as part of the user experience while communicating with the user, and/or any other form of theme, as discussed herein, and/or as known in the art at the time of filing, and/or as developed after the time of filing, according to various embodiments.

According to various embodiments, USER ASSISTANCE 122 includes various user experience components for providing assistance to a user, according to one embodiment. Examples of USER ASSISTANCE 122 include, but are not limited to, one or more of an instant message dialog box, an offer to call the user, a fax number, a mailing address, a phone number to which text messages may be transmitted, a URL or other link, an address to a live human service provider that is local to the geographic location of the user, and/or any other form of user assistance, as discussed herein, and/or as known in the art at the time of filing, and/or as developed after the time of filing.

In one embodiment, PROFILES 123 represents a repository, data structure, or database of user data that is grouped based on commonalities between the user's and/or users' data, including the user's and/or users' emotional state data. In one embodiment, PROFILES 123 are grouped based on criteria such as marital status, approximate income range, job title, age ranges, homeownership status, employment status, zip code, level of education, etc. Each profile of PROFILES 123 can be associated with a particular set of user data variables, in one embodiment. The particular set of user data variables can be associated with a particular sequence of topics in the question and/or suggestion pool, with a particular theme, with a particular type of user assistance, and/or with one or more particular pictures, according to one embodiment. Accordingly, the production environment may associate a user with a particular one of PROFILES 123 in order to indirectly assign the user to a particular sequence of topics in QUESTION AND/OR SUGGESTION POOL 119, according to one embodiment.

In one embodiment, SELECTED INTERCHANGEABLE ANALYTICS MODULE 113 uses one or more of QUESTION AND/OR SUGGESTION POOL 119, PICTURES 120, THEMES 121, USER ASSISTANCE 122, and PROFILES 123 to select one or more user experience components as SELECTED USER EXPERIENCE COMPONENT 117. According to one embodiment, the components within USER EXPERIENCE SYSTEM 111 communicate with SELECTED INTERCHANGEABLE ANALYTICS MODULE 113 using API functions, routines, and/or calls. However, according to another embodiment, SELECTED INTERCHANGEABLE ANALYTICS MODULE 113 and USER EXPERIENCE CUSTOMIZATION ENGINE 112 can use COMMON STORE 124 for sharing, communicating, or otherwise delivering information between different features or components within USER EXPERIENCE SYSTEM 111. In one embodiment, COMMON STORE 124 includes, but is not limited to, USER DATA 116, ANALYTIC DATA 118, and USER EXPERIENCE CUSTOMIZATION ENGINE DATA 125. In one embodiment, SELECTED INTERCHANGEABLE ANALYTICS MODULE 113 can be configured to store information and retrieve information from COMMON STORE 124 independent of information retrieved from and stored to COMMON STORE 124 by USER EXPERIENCE CUSTOMIZATION ENGINE 112. In addition to SELECTED INTERCHANGEABLE ANALYTICS MODULE 113 and USER EXPERIENCE CUSTOMIZATION ENGINE 112, other components within USER EXPERIENCE SYSTEM 111 and other computer environments may be granted access to COMMON STORE 124 to facilitate communications with SELECTED INTERCHANGEABLE ANALYTICS MODULE 113 and/or USER EXPERIENCE CUSTOMIZATION ENGINE 112, according to one embodiment.

In various embodiments, USER EXPERIENCE CUSTOMIZATION ENGINE 112 can be configured to synchronously or asynchronously retrieve, apply, and present SELECTED USER EXPERIENCE COMPONENT 117. In one embodiment, USER EXPERIENCE CUSTOMIZATION ENGINE 112 can be configured to submit USER DATA 116 to SELECTED INTERCHANGEABLE ANALYTICS MODULE 113 or submit another request to SELECTED INTERCHANGEABLE ANALYTICS MODULE 113 and wait to receive a response from SELECTED INTERCHANGEABLE ANALYTICS MODULE 113 before continuing to interact with the user. In one embodiment, USER EXPERIENCE CUSTOMIZATION ENGINE 112 can alternatively be configured to submit USER DATA 116 to SELECTED INTERCHANGEABLE ANALYTICS MODULE 113 or submit another request to SELECTED INTERCHANGEABLE ANALYTICS MODULE 113 and concurrently continue functioning/operating without waiting for a response from SELECTED INTERCHANGEABLE ANALYTICS MODULE 113.

In other words, USER EXPERIENCE CUSTOMIZATION ENGINE 112 can be configured to asynchronously continue to operate independent of SELECTED INTERCHANGEABLE ANALYTICS MODULE 113 even though SELECTED INTERCHANGEABLE ANALYTICS MODULE 113 is processing information that is needed by USER EXPERIENCE CUSTOMIZATION ENGINE 112. In one embodiment, USER EXPERIENCE CUSTOMIZATION ENGINE 112 then incorporates information from SELECTED INTERCHANGEABLE ANALYTICS MODULE 113 as SELECTED INTERCHANGEABLE ANALYTICS MODULE 113 makes the information available. In one embodiment, a user experience is presented to the user for a time prior to executing SELECTED INTERCHANGEABLE ANALYTICS MODULE 113. In other embodiments, USER EXPERIENCE CUSTOMIZATION ENGINE 112 calls the analytics module at any time while the user is interacting with the interactive software system.

In one embodiment, as discussed below, the selection of SELECTED INTERCHANGEABLE ANALYTICS MODULE 113 from, as an example, a pool of interchangeable analytics modules, such as INTERCHANGEABLE ANALYTICS MODULES 152, 153, 154, and 155, is made based, at least in part, on user data associated with a user during the user's interaction with the user experience initially presented to the user. In one embodiment, as discussed below, the selection of SELECTED INTERCHANGEABLE ANALYTICS MODULE 113 from, as an example, a pool of interchangeable analytics modules, such as INTERCHANGEABLE ANALYTICS MODULES 152, 153, 154, and 155, is made based, at least in part, on emotional state data associated with a user during the user's initial and/or preliminary interaction with an interactive software system. In addition, as also discussed below, in one embodiment, the selection of SELECTED INTERCHANGEABLE ANALYTICS MODULE 113, and/or exchange of SELECTED INTERCHANGEABLE ANALYTICS MODULE 113 for another selected interchangeable analytics module from, as an example, a pool of interchangeable analytics modules, such as INTERCHANGEABLE ANALYTICS MODULES 152, 153, 154, and 155, is made based, at least in part, on any, or all, of USER DATA 116, during any part of the user's interaction with the user experience.

Alternatively, ANALYTICS MODULE SELECTION ENGINE 126 can be configured to automatically and/or dynamically retrieve and implement an interchangeable analytics module into USER EXPERIENCE SYSTEM 111 based on information about the user, such as, but not limited to, USER DATA 116, according to one embodiment. For example, ANALYTICS MODULE SELECTION ENGINE 126 can receive USER DATA 116 from USER EXPERIENCE CUSTOMIZATION ENGINE 112, according to one embodiment. In one embodiment, ANALYTICS MODULE SELECTION ENGINE 126 can then use USER DATA 116 to retrieve PRIOR USER DATA 151 from INTERACTIVE SOFTWARE SYSTEM SUPPORT COMPUTING ENVIRONMENT 150. In one embodiment, PRIOR USER DATA 151 is user data obtained during or prior to a user's current interaction with an interactive software system.

In one embodiment, ANALYTICS MODULE SELECTION ENGINE 126 is configured to use PRIOR USER DATA 151 to determine which one of a number of analytics modules to incorporate in USER EXPERIENCE SYSTEM 111, according to one embodiment. As illustrated, INTERACTIVE SOFTWARE SYSTEM SUPPORT COMPUTING ENVIRONMENT 150 can include a number of different interchangeable analytics modules, for example, INTERCHANGEABLE ANALYTICS MODULE 152, INTERCHANGEABLE ANALYTICS MODULE 153, INTERCHANGEABLE ANALYTICS MODULE 154, and INTERCHANGEABLE ANALYTICS MODULE 155, according to one embodiment. Each of INTERCHANGEABLE ANALYTICS MODULES 152, 153, 154, and 155 incorporates a different algorithm for generating ANALYTIC DATA 118 and selecting SELECTED USER EXPERIENCE COMPONENT 117 based on USER DATA 116, according to one embodiment. As discussed above, INTERCHANGEABLE ANALYTICS MODULES 152, 153, 154, and 155 can utilize a number analysis algorithms and techniques, such as predictive models and collaborative filters, according to various embodiments.

Selecting SELECTED USER EXPERIENCE COMPONENT 117 in anticipation of the user's expected emotional state may advantageously invoke feelings of trust and/or personal connection from the user towards USER EXPERIENCE SYSTEM 111. Consequently, in contrast to traditional user experiences and interactive software systems, the user is provided with a personal, responsive, and customized user experience, according to one embodiment. Because the user experience directly meets the needs of the user, this, in turn, allows for a drastic improvement in user experience and customer service. As a result, embodiments of the present disclosure allow for interactive software systems to provide users with an efficient and effective service.

In one embodiment, USER DATA 116 and/or PRIOR USER DATA 151 can be used by USER EXPERIENCE CUSTOMIZATION ENGINE 112 and/or SELECTED INTERCHANGEABLE ANALYTICS MODULE 113 to associate a user with a particular predetermined profile, e.g., with a set of criteria or with a group of users who share one or more characteristics in common with the user. However, in other embodiments, a user's answers to one or more initial questions and/or suggestions can be used by SELECTED INTERCHANGEABLE ANALYTICS MODULE 113 to identify peers of the user, e.g., other users who share or who have shared similar emotional state data and/or who share similar user data characteristics. In one embodiment, SELECTED INTERCHANGEABLE ANALYTICS MODULE 113, or another component within USER EXPERIENCE SYSTEM 111, identify the user experiences that were commonly relevant to the peers of the user and can select the user experience components associated with those user experiences that were more relevant to the peers of the user. This up-to-date analysis simplifies the analysis of USER DATA 116 while improving the likelihood that USER EXPERIENCE CUSTOMIZATION ENGINE 112 accurately selects user experience components that are likely to be relevant to the user, based on the user's peers, according to one embodiment.

Unlike the user experience associated with traditional interactive software systems, USER EXPERIENCE SYSTEM 111 can reduce confusion, frustration, and trust issues of users by selecting user experience components to present the user with a user experience responsive to the user's dynamic emotional state. As a result, the features and techniques described herein are, in many ways, superior to the service received from a human service provider. For example, human error associated with a human service provider is eliminated, the hours of availability of the human service provider become irrelevant, the daily number of customers is not limited by the number of people a human service provider is able to visit within a daily basis, and the system and method disclosed herein is unaffected by emotion, fatigue, stress, or other external factors that may be inherent in a human service provider.

Process

In accordance with one embodiment of a process for using emotional state data to tailor the user experience of an interactive software system, an interactive software system is provided, through which a user can be provided with one or more user experience components that are generated and/or combined to provide a user experience.

In accordance with one embodiment, user experience components are defined. In one embodiment, combinations of user experience components are defined. In one embodiment, user experience component data representing one or more of the one or more user experience components is generated.

In one embodiment, emotional state data to be obtained and analyzed is defined. In one embodiment, emotional state data is data representing a user's physiological manifestations of emotion. In one embodiment, emotional state data is data representing a user's own characterization of his or her emotional state. In one embodiment, emotional state data is data representing historical user data and/or data associated with a segment of users having characteristics comparable to the user. In one embodiment, emotional state threshold parameter data is defined for each defined type of emotional state data to be obtained and analyzed. In one embodiment, emotional state threshold parameter data is a set of defined physiological data to determine whether a user is in a certain emotional state. As discussed herein, by gathering emotional state data, the interactive software system can gather data about the emotional states of its users and compare that data to data representing defined emotional state threshold parameters to determine when a user's emotional state is approaching or has reached a point that warrants corrective action. In one embodiment, emotional state threshold parameter data is generated representing the defined state threshold parameters.

In one embodiment, emotional state data is received or otherwise obtained. In one embodiment, the emotional state data is received via hardware associated with a computing system used to implement at least part of an interactive software system. For example, in one embodiment, emotional state data relating to the user's heart beat is received via a heart rate monitor associated with a computing system used to implement at least part of an interactive software system.

In one embodiment, one or more analytics modules are provided. In one embodiment, each of the one or more analytics modules is used to implement at least part of one or more associated analytics algorithms. In one embodiment, the received emotional state data is provided to one or more of the one or more analytics modules.

Once provided to the one or more analytics modules, the emotional state data is analyzed to identify the user's emotional state. In one embodiment, the emotional state data is analyzed and/or compared with emotional state threshold parameter data representing the emotional state threshold parameter associated with the type of emotional state data obtained. In various embodiments, the emotional state data is analyzed and/or compared with the associated emotional state parameter data to determine that the user is in an undesirable emotional state, that the user's emotional state is deteriorating, and/or that the user is approaching an undesirable emotional state.

In one embodiment, based at least in part on the analysis of the received emotional state data and the associated emotional state threshold parameter data, the emotional state of the user is determined. Depending on the user's emotional state, the user experience can be dynamically adapted by selecting appropriate user experience components. According to various embodiments, user experience components or combinations of user experience components are selected to dynamically modify a user experience in response to a user's emotional state. In one embodiment, user experience components are selected based upon a predicted emotional state. For example, if the user is in a stressed emotional state, user experience components and/or combinations of user experience components thought to have a calming effect are selected.

In one embodiment, the selected user experience components are presented to the user. By presenting selected user experience components adapted to the emotional state of the user, an interactive software system's user experience can be customized to address a user's emotional state, preserve a user's emotional state, and/or change a user's emotional state. By providing user experience components dynamically selected to generate a user experience adapted to a user and a user's emotional state, an interactive software system provides a more effective and efficient user experience to its users, which allows the interactive software system to provide better customer service and retain more of its customers. Furthermore, when user experience components are dynamically adapted to a user, the user is able to have a more efficient, pleasant, and meaningful user experience.

Figure 2:
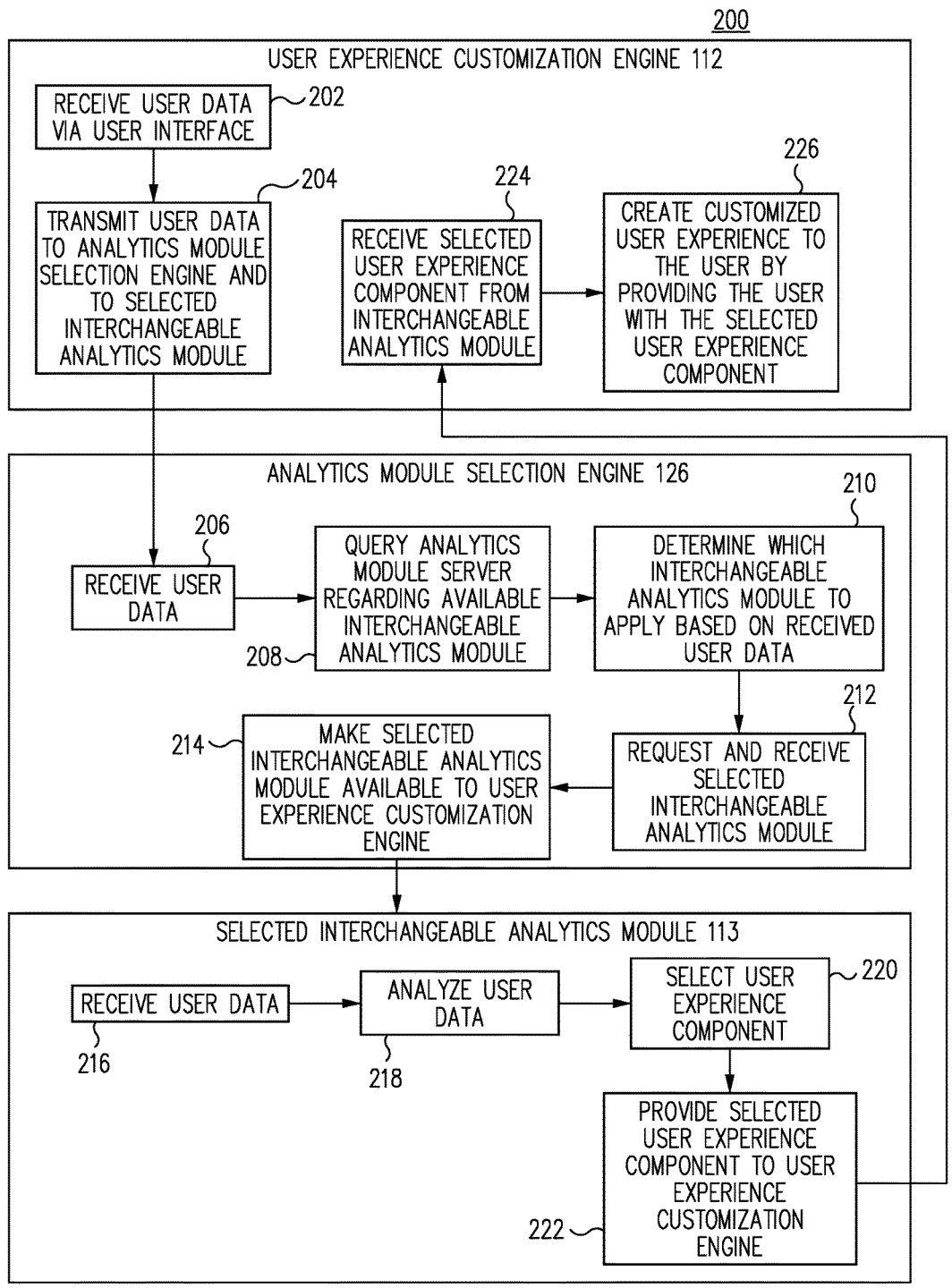
FIG. 2 is a block diagram of a process for providing an interactive software system with a user experience adapted to a user's emotional state, in accordance with one embodiment.

FIG. 2 illustrates a functional flow diagram of a process 200 for providing an interactive software system with a user experience adapted to a user's emotional state, in accordance with one embodiment. Although a particular sequence of events is described hereafter, more or less events may be included in the process 200, according to various embodiments.

At block 202, in one embodiment, USER EXPERIENCE CUSTOMIZATION ENGINE 112 receives user data via a user interface.

In one embodiment, at block 204, USER EXPERIENCE CUSTOMIZATION ENGINE 112 transmits the user data to ANALYTICS MODULE SELECTION ENGINE 126 and to SELECTED INTERCHANGEABLE ANALYTICS MODULE 113.

At block 206, in one embodiment, ANALYTICS MODULE SELECTION ENGINE 126 receives the user data from USER EXPERIENCE CUSTOMIZATION ENGINE 112.

At block 208, ANALYTICS MODULE SELECTION ENGINE 126 queries an analytics module server regarding available interchangeable analytics modules, according to one embodiment. In various embodiments, the analytics module server may be one or more databases that are included within the interactive software system computing environment or it may be one or more databases that are external to the interactive software system computing environment.

At block 210, ANALYTICS MODULE SELECTION ENGINE 126 determines which interchangeable analytics module to select based on the received user data, in one embodiment.

In one embodiment, at block 212, ANALYTICS MODULE SELECTION ENGINE 126 requests and receives SELECTED INTERCHANGEABLE ANALYTICS MODULE 113.

At block 214, in one embodiment, ANALYTICS MODULE SELECTION ENGINE 126 makes SELECTED INTERCHANGEABLE ANALYTICS MODULE 113 available to USER EXPERIENCE CUSTOMIZATION ENGINE 112. For example, ANALYTICS MODULE SELECTION ENGINE 126 can copy SELECTED INTERCHANGEABLE ANALYTICS MODULE 113 into a particular range of memory addresses within a computing environment that are used by a user experience system to execute SELECTED INTERCHANGEABLE ANALYTICS MODULE 113, according to one embodiment. In one embodiment, ANALYTICS MODULE SELECTION ENGINE 126 can copy SELECTED INTERCHANGEABLE ANALYTICS MODULE 113 into a memory location that is accessible by the other components of the user experience system, and ANALYTICS MODULE SELECTION ENGINE 126 can update a pointer table or other data structure used by the user experience system so that calls, requests, and/or routines that rely upon SELECTED INTERCHANGEABLE ANALYTICS MODULE 113 may be properly directed to the newly installed SELECTED INTERCHANGEABLE ANALYTICS MODULE 113, according to one embodiment.

In one embodiment, at block 216, SELECTED INTERCHANGEABLE ANALYTICS MODULE 113 receives the user data. According to various embodiments, SELECTED INTERCHANGEABLE ANALYTICS MODULE 113 can receive the user data from USER EXPERIENCE CUSTOMIZATION ENGINE 112 or from ANALYTICS MODULE SELECTION ENGINE 126 after SELECTED INTERCHANGEABLE ANALYTICS MODULE 113 has been installed.

At block 218, SELECTED INTERCHANGEABLE ANALYTICS MODULE 113 analyzes the user data, according to one embodiment. As described above, various analysis algorithms discussed herein, known in the art at the time of filing, and/or as developed after the time of filing may be applied to the user data, according to one embodiment. In one embodiment, emotional state threshold parameter data is applied to the user data.

At block 220, SELECTED INTERCHANGEABLE ANALYTICS MODULE 113 selects a user experience component, according to one embodiment. The selected user experience component can include, but is not limited to, one or more of the following: data entry; question and/or suggestion submission; interview process; individualized user interview questions and/or suggestions and question and/or suggestion sequences; user interfaces; interface displays; sub-displays; images; side bar displays; pop-up displays; alarms; music; backgrounds; avatars; highlighting mechanisms; icons; assistance resources; user recommendations; supplemental actions and recommendations; and/or any other components that individually, or in combination, create a user experience, as discussed herein, and/or as known in the art at the time of filing, and/or as developed after the time of filing.

The selected user experience component is selected based on the received user data and the analysis of the user data, according to one embodiment.

At block 222, SELECTED INTERCHANGEABLE ANALYTICS MODULE 113 provides the selected user experience component to USER EXPERIENCE CUSTOMIZATION ENGINE 112, according to one embodiment. According to various embodiments, SELECTED INTERCHANGEABLE ANALYTICS MODULE 113 can be configured to communicate with USER EXPERIENCE CUSTOMIZATION ENGINE 112 using an API, a common data store, or other techniques.

At block 224, USER EXPERIENCE CUSTOMIZATION ENGINE 112 receives the selected user experience component from SELECTED INTERCHANGEABLE ANALYTICS MODULE 113, according to one embodiment.

At block 226, USER EXPERIENCE CUSTOMIZATION ENGINE 112 creates a customized user experience to the user by providing the selected user experience component to the user, according to one embodiment. In one embodiment, USER EXPERIENCE CUSTOMIZATION ENGINE 112 can provide the selected user experience component to the user synchronously, i.e., only after certain data is received from SELECTED INTERCHANGEABLE ANALYTICS MODULE 113. In one embodiment, USER EXPERIENCE CUSTOMIZATION ENGINE 112 can provide selected user experience component to the user asynchronously, i.e., concurrent with data analysis being performed by SELECTED INTERCHANGEABLE ANALYTICS MODULE 113. In one embodiment, providing the selected user experience component to the user based on the user data transforms the user experience from a default, generic user experience into an individualized or customized user experience. This, in turn, allows for significant improvement to the technical fields of user experience and customer service. Furthermore, by preventing waste of processing cycles and communication bandwidth on users who would have otherwise left the system, the present disclosure allows for significant improvement to the technical fields of data collection and data processing. As a result, embodiments of the present disclosure allow for improved processor performance, more efficient use of memory access and data storage capabilities, reduced communication channel bandwidth utilization, and faster communications connections. Consequently, computing and communication systems implementing and/or providing the embodiments of the present disclosure are transformed into faster and more operationally efficient devices and systems.

Although a particular sequence is described herein for the execution of the process 200, other sequences can also be implemented, according to other embodiments.

Figure 3:
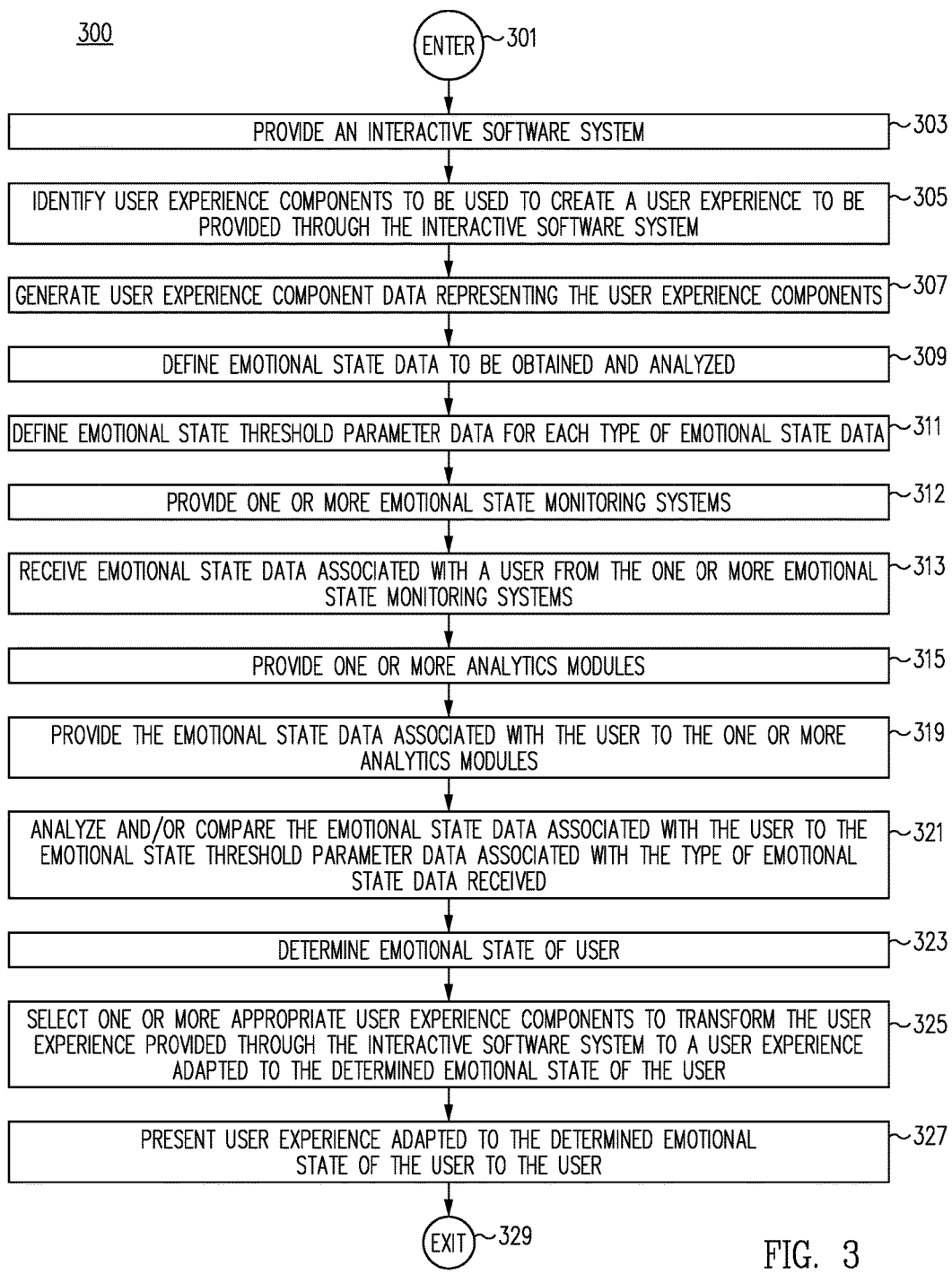
FIG. 3 is a flow diagram for using emotional state data to individualize the user experience provided through the interactive software system in accordance with one embodiment.

FIG. 3 is a flow chart representing one example of a process 300 for using emotional state data to tailor the user experience of an interactive software system in accordance with one embodiment.

As seen in FIG. 3, in one embodiment, process 300 for using emotional state data to tailor the user experience of an interactive software system begins at ENTER OPERATION 301 and process flow proceeds to PROVIDE AN INTERACTIVE SOFTWARE SYSTEM OPERATION 303.

In one embodiment, at PROVIDE AN INTERACTIVE SOFTWARE SYSTEM OPERATION 303, an interactive software system is provided for use by one or more users. In various embodiments, the interactive software system of PROVIDE AN INTERACTIVE SOFTWARE SYSTEM OPERATION 303 is any interactive software system as discussed herein, as known in the art at the time of filing, and/or as developed after the time of filing.

For example, in various embodiments, the interactive software system provided at PROVIDE AN INTERACTIVE SOFTWARE SYSTEM OPERATION 303 can be, but is not limited to, any software system that provides an interactive user experience to its users and is implemented on a computing system, accessed through one or more servers, accessed through a network, accessed through a cloud, and/or provided through any computing system or by any means as discussed herein, as known in the art at the time of filing, and/or as developed after the time of filing.

As noted above, the interactive software system provided at PROVIDE AN INTERACTIVE SOFTWARE SYSTEM OPERATION 303 can be, but is not limited to, a web-based, online, and/or computing system implemented personal and/or business tax preparation systems; web-based, online, and/or computing system implemented personal and/or business financial management systems, services, packages, programs, modules, or applications; web-based, online, and/or computing system implemented personal and/or business management systems, services, packages, programs, modules, or applications; web-based, online, and/or computing system implemented personal and/or business accounting and/or invoicing systems, services, packages, programs, modules, or applications; and various other personal and/or business electronic data management systems, services, packages, programs, modules, or applications, whether known at the time of filing or as developed later.

Specific examples of interactive software systems include, but are not limited to the following: TurboTax™ available from Intuit, Inc. of Mountain View, Calif.; TurboTax Online™ available from Intuit, Inc. of Mountain View, Calif.; Quicken™, available from Intuit, Inc. of Mountain View, Calif.; Quicken Online™, available from Intuit, Inc. of Mountain View, Calif.; QuickBooks™, available from Intuit, Inc. of Mountain View, Calif.; QuickBooks Online™, available from Intuit, Inc. of Mountain View, Calif.; Mint™, available from Intuit, Inc. of Mountain View, Calif.; Mint Online™, available from Intuit, Inc. of Mountain View, Calif.; and/or various other software systems discussed herein, and/or known to those of skill in the art at the time of filing, and/or as developed after the time of filing.

As noted above, the effectiveness of the interactive software system of PROVIDE AN INTERACTIVE SOFTWARE SYSTEM OPERATION 303 depends upon the interactive software system's ability to provide a meaningful user experience to its users while avoiding stressing, frustrating, and/or alienating the user. Nonetheless, the user experiences currently presented to users are typically generic and static. Using currently available interactive software systems, the user experience presented to a user is not customized based on the user's current or predicted emotional state. Therefore, currently available interactive software systems run the risk of alienating users by presenting an inappropriate user experience. As discussed herein, however, the disclosed embodiments of process 300 for using emotional state data to tailor the user experience of an interactive software system address these shortcomings by providing a mechanism by which an interactive software system may dynamically adjust the user experience it provides to a user based upon the user's current or predicted emotional state. As a result, the fields of user experience, customer service, communication, and interactive software systems are significantly improved by implementing the various embodiments of process 300 for using emotional state data to tailor the user experience of an interactive software system.

In one embodiment, once the interactive software system is provided at PROVIDE AN INTERACTIVE SOFTWARE SYSTEM OPERATION 303, process flow proceeds to IDENTIFY USER EXPERIENCE COMPONENTS TO BE USED TO CREATE A USER EXPERIENCE TO BE PROVIDED THROUGH THE INTERACTIVE SOFTWARE SYSTEM OPERATION 305. In one embodiment, at IDENTIFY USER EXPERIENCE COMPONENTS TO BE USED TO CREATE A USER EXPERIENCE TO BE PROVIDED THROUGH THE INTERACTIVE SOFTWARE SYSTEM OPERATION 305, user experience components that can be used and/or combined to create a user experience that will be provided through the interactive software system are identified.

As discussed herein, a user experience of IDENTIFY USER EXPERIENCE COMPONENTS TO BE USED TO CREATE A USER EXPERIENCE TO BE PROVIDED THROUGH THE INTERACTIVE SOFTWARE SYSTEM OPERATION 305 includes the practical, experiential, affective, significant, and/or valuable aspects of human/software interaction.

In one embodiment, the user experience components of IDENTIFY USER EXPERIENCE COMPONENTS TO BE USED TO CREATE A USER EXPERIENCE TO BE PROVIDED THROUGH THE INTERACTIVE SOFTWARE SYSTEM OPERATION 305 include the various elements that make up a user experience. In various embodiments, the user experience components of IDENTIFY USER EXPERIENCE COMPONENTS TO BE USED TO CREATE A USER EXPERIENCE TO BE PROVIDED THROUGH THE INTERACTIVE SOFTWARE SYSTEM OPERATION 305 include, but are not limited to, individualized user interview questions and question sequences, user interfaces, interface displays, sub-displays, images, side bar displays, pop-up displays, alarms, music, backgrounds, avatars, highlighting mechanisms, icons, assistance resources, user recommendations, supplemental actions and recommendations, and/or any other components that individually, or in combination, create a user experience, as discussed herein, and/or as known in the art at the time of filing, and/or as developed after the time of filing.

In one embodiment, once the user experience components to be used to create a user experience to be provided through the interactive software system are identified at IDENTIFY USER EXPERIENCE COMPONENTS TO BE USED TO CREATE A USER EXPERIENCE TO BE PROVIDED THROUGH THE INTERACTIVE SOFTWARE SYSTEM OPERATION 305, process flow proceeds to GENERATE USER EXPERIENCE COMPONENT DATA REPRESENTING THE USER EXPERIENCE COMPONENTS OPERATION 307.

In one embodiment, at GENERATE USER EXPERIENCE COMPONENT DATA REPRESENTING THE USER EXPERIENCE COMPONENTS OPERATION 307, user experience component data, representing user experience components such as individualized user interview questions and question sequences, user interfaces, interface displays, sub-displays, images, side bar displays, pop-up displays, alarms, music, backgrounds, avatars, highlighting mechanisms, icons, assistance resources, user recommendations, supplemental actions and recommendations, and/or any other components that individually, or in combination, create a user experience, as discussed herein, and/or as known in the art at the time of filing, and/or as developed after the time of filing is generated through, or provided to, the interactive software system.

As discussed below, in one embodiment, the user experience component data of GENERATE USER EXPERIENCE COMPONENT DATA REPRESENTING THE USER EXPERIENCE COMPONENTS OPERATION 307 is selected at SELECT ONE OR MORE APPROPRIATE USER EXPERIENCE COMPONENTS TO TRANSFORM THE USER EXPERIENCE PROVIDED THROUGH THE INTERACTIVE SOFTWARE SYSTEM TO A USER EXPERIENCE ADAPTED TO THE DETERMINED EMOTIONAL STATE OF THE USER OPERATION 325.

In one embodiment, the user experience component data of GENERATE USER EXPERIENCE COMPONENT DATA REPRESENTING THE USER EXPERIENCE COMPONENTS OPERATION 307 is machine readable representations of user experience components.

In one embodiment, the user experience component data of GENERATE USER EXPERIENCE COMPONENT DATA REPRESENTING THE USER EXPERIENCE COMPONENTS OPERATION 307 is a listing of multiple optical characters and/or patterns and multiple arrangements of optical characters and/or patterns.

In one embodiment, once user experience component data representing the user experience components is generated at GENERATE USER EXPERIENCE COMPONENT DATA REPRESENTING THE USER EXPERIENCE COMPONENTS OPERATION 307, process flow proceeds to DEFINE EMOTIONAL STATE DATA TO BE OBTAINED AND ANALYZED OPERATION 309.

In one embodiment, the emotional state data of DEFINE EMOTIONAL STATE DATA TO BE OBTAINED AND ANALYZED OPERATION 309 is representative of one or more of the following emotional states: a tense emotional state; a nervous emotional state; a stressed emotional state; an upset emotional state; a frustrated emotional state; a sad emotional state; a depressed emotional state; a bored emotional state; a fatigued emotional state; an alert emotional state; an excited emotional state; an elated emotional state; a happy emotional state; a contented emotional state; a serene emotional state; a relaxed emotional state; and/or a calm emotional state.

As discussed above, in various embodiments, the emotional state data of DEFINE EMOTIONAL STATE DATA TO BE OBTAINED AND ANALYZED OPERATION 309 includes, but is not limited to, data acquired from the user's own characterization of his or her emotional state; data acquired from historical user data; data acquired from a segment of users having characteristics comparable to the user; data acquired from measuring a user's heart beat; data acquired from measuring a user's eye rotation; data acquired from measuring a user's perspiration; data acquired from measuring a user's respiration; data acquired from measuring a user's oxygen saturation; data acquired from measuring a user's blood pressure; data acquired from measuring a user's skin temperature; data acquired from measuring a user's muscle tension; data acquired from measuring a user's neural activity; data acquired from measuring a user's eye blinking; data acquired from measuring one or more of a user's facial expressions; data acquired from measuring a user's voice and/or speech; and/or data acquired from measuring a user's interaction with hardware associated with the interactive software system.

In one embodiment, the emotional state data of DEFINE EMOTIONAL STATE DATA TO BE OBTAINED AND ANALYZED OPERATION 309 is data acquired from the user's own characterization of his or her emotional state. For example, in one embodiment, the user is presented with a pop-up requesting information about the user's emotional state. Then, in one embodiment, the emotional state data of DEFINE EMOTIONAL STATE DATA TO BE OBTAINED AND ANALYZED OPERATION 309 is the data provided by the user via the pop-up. In one embodiment, the emotional state data of DEFINE EMOTIONAL STATE DATA TO BE OBTAINED AND ANALYZED OPERATION 309 is data associated with the user's attempts to seek assistance resources via the interactive software system.

In one embodiment, the emotional state data of DEFINE EMOTIONAL STATE DATA TO BE OBTAINED AND ANALYZED OPERATION 309 is historical user data, that is, data associated with the user's previous interactions with the interactive software system. For example, in one embodiment, if a user of a financial management service associated with an interactive software system requests information about his or her restaurant budget to determine whether it is feasible to eat out that evening, the financial management service relies on historical user data to estimate the amount of money the user spends when eating out. Then, in one embodiment, if the user does not have enough money in his or her budget to eat out, the financial management service associated with an interactive software system predicts the emotional state of the user and selects user experience components to tailor the user experience accordingly.

In one embodiment, the emotional state data of DEFINE EMOTIONAL STATE DATA TO BE OBTAINED AND ANALYZED OPERATION 309 is data associated with a segment of users having characteristics comparable to the user. For example, in one embodiment, if a user of a financial management service associated with an interactive software system requests information about his or her restaurant budget to determine whether it is feasible to go to the movies that evening, the financial management service relies on data associated with a segment of users having characteristics comparable to the user to estimate the amount of money the user will spend when going to the movies. Then, in one embodiment, if the user does not have enough money in his or her budget to go to the movies, the financial management service associated with an interactive software system predicts the emotional state of the user and selects user experience components to tailor the user experience accordingly.

In one embodiment, the emotional state data of DEFINE EMOTIONAL STATE DATA TO BE OBTAINED AND ANALYZED OPERATION 309 represents more than one emotional state.

Once the emotional state data to be obtained and analyzed is defined at DEFINE EMOTIONAL STATE DATA TO BE OBTAINED AND ANALYZED OPERATION 309, process flow proceeds to DEFINE EMOTIONAL STATE THRESHOLD PARAMETER DATA FOR EACH TYPE OF EMOTIONAL STATE DATA OPERATION 311.

One or more of the embodiments disclosed herein utilize and/or incorporate theories and relationships discovered through analysis of data obtained from a user, multiple users, and/or general study of human emotion. Consequently, the emotional state threshold parameter data of DEFINE EMOTIONAL STATE THRESHOLD PARAMETER DATA FOR EACH TYPE OF EMOTIONAL STATE DATA OPERATION 311 represents an ordering of emotional state data. In one embodiment, emotional state threshold parameter data is defined for one type of emotional state data. In one embodiment, emotional state threshold parameter data are defined for a combination of types of emotional state data.

In one embodiment, the rate of a user's heart beat is obtained to provide data about the user's emotional state. Emotional state threshold parameter data provides a means of analyzing that emotional state data. For example, in one embodiment, a heart rate emotional state threshold parameter associated with a user's heart beat is defined. In one embodiment, the emotional state threshold parameter may be defined to provide that a user with a heartbeat of over 100 beats per minute is stressed.

In one embodiment, a heart rate variability level emotional state threshold parameter associated with a user's heart beat is defined.

In one embodiment, a scan path emotional state threshold parameter associated with a user's eye rotation is defined. In one embodiment, a fixation period emotional state threshold parameter associated with a user's eye rotation is defined such that if the fixation period emotional state threshold parameter is exceeded and/or is not met, then the user is determined to be in one or more of the defined emotional states.

In one embodiment, a skin conductance level emotional state threshold parameter associated with a user's perspiration is defined such that if the skin conductance level emotional state threshold parameter is exceeded and/or is not met, then the user is determined to be in one or more of the defined emotional states.

In one embodiment, a respiration rate emotional state threshold parameter associated with a user's respiration is defined such that if the respiration rate emotional state threshold parameter is exceeded and/or is not met, then the user is determined to be in one or more of the defined emotional states.

In one embodiment, an oxygen saturation level emotional state threshold parameter associated with a user's oxygen saturation is defined such that if the oxygen saturation level emotional state threshold parameter is exceeded and/or is not met, then the user is determined to be in one or more of the defined emotional states. In one embodiment, a blood pressure level emotional state threshold parameter associated with a user's blood pressure is defined such that if the blood pressure level emotional state threshold parameter is exceeded and/or is not met, then the user is determined to be in one or more of the defined emotional states.

In one embodiment, a skin temperature emotional state threshold parameter associated with a user's skin temperature is defined such that if the skin temperature emotional state threshold parameter is exceeded and/or is not met, then the user is determined to be in one or more of the defined emotional states.

In one embodiment, a muscle tension level emotional state threshold parameter associated with a user's muscle tension is defined such that if the muscle tension level emotional state threshold parameter is exceeded and/or is not met, then the user is determined to be in one or more of the defined emotional states.

In one embodiment, a neural activity level emotional state threshold parameter associated with a user's neural activity is defined such that if the neural activity level emotional state threshold parameter is exceeded and/or is not met, then the user is determined to be in one or more of the defined emotional states.

In one embodiment, an eye blink rate emotional state threshold parameter associated with a user's eye blinking is defined such that if the eye blink rate emotional state threshold parameter is exceeded and/or is not met, then the user is determined to be in one or more of the defined emotional states. In one embodiment, a facial muscle movement emotional state threshold parameter associated with a user's facial expression is defined such that if the facial muscle movement emotional state threshold parameter is exceeded and/or is not met, then the user is determined to be in one or more of the defined emotional states.

In one embodiment, an acoustic characteristics emotional state threshold parameter associated with a user's voice and/or speech is defined such that if the acoustic characteristics emotional state threshold parameter is exceeded and/or is not met, then the user is determined to be in one or more of the defined emotional states.

In one embodiment, a contact pressure emotional state threshold parameter associated with a user's interaction with hardware associated with the interactive software system is defined such that if the contact pressure emotional state threshold parameter is exceeded and/or is not met, then the user is determined to be in one or more of the defined emotional states. In one embodiment, a contact rate emotional state threshold parameter associated with a user's interaction with hardware associated with the interactive software system is defined such that if the contact rate emotional state threshold parameter associated is exceeded and/or is not met, then the user is determined to be in one or more of the defined emotional states.

Once emotional state threshold parameter data for each type of emotional state data is defined at DEFINE EMOTIONAL STATE THRESHOLD PARAMETER DATA FOR EACH TYPE OF EMOTIONAL STATE DATA OPERATION 311, process flow proceeds to PROVIDE ONE OR MORE EMOTIONAL STATE MONITORING SYSTEMS OPERATION 312.

In various embodiments, the emotional state monitoring systems of PROVIDE ONE OR MORE EMOTIONAL STATE MONITORING SYSTEMS OPERATION 312, include, but are not limited to, one or more of the following: a heart rate monitor associated with an interactive software system, an eye tracker associated with an interactive software system; an emotional state monitoring system associated with an interactive software system to measure a user's skin conductance level; an emotional state monitoring system associated with an interactive software system to measure a user's respiration rate; an emotional state monitoring system associated with an interactive software system to measure a user's oxygen saturation level; an emotional state monitoring system associated with an interactive software system to measure a user's blood pressure level; an emotional state monitoring system associated with an interactive software system to measure a user's skin temperature; an emotional state monitoring system associated with an interactive software system to measure a user's muscle tension level; an emotional state monitoring system associated with an interactive software system to measure a user's neural activity; an emotional state monitoring system associated with an interactive software system to measure a user's eye blink rate; an emotional state monitoring system associated with an interactive software system to measure a user's facial muscle movement; an emotional state monitoring system associated with an interactive software system to measure a user's acoustic characteristics; and/or an emotional state monitoring system associated with an interactive software system to measure a user's interaction with hardware associated with an interactive software system.

In various embodiments, the emotional state monitoring systems of PROVIDE ONE OR MORE EMOTIONAL STATE MONITORING SYSTEMS OPERATION 312 include any emotional state monitoring system as described herein, as known in the art at the time of filing, and/or as developed after filing.

Once one or more emotional state monitoring systems are provided at PROVIDE ONE OR MORE EMOTIONAL STATE MONITORING SYSTEMS OPERATION 312, process flow proceeds to RECEIVE EMOTIONAL STATE DATA ASSOCIATED WITH A USER FROM THE ONE OR MORE EMOTIONAL STATE MONITORING SYSTEMS OPERATION 313.

In various embodiments, the emotional state data of RECEIVE EMOTIONAL STATE DATA ASSOCIATED WITH A USER FROM THE ONE OR MORE EMOTIONAL STATE MONITORING SYSTEMS OPERATION 313 includes, but is not limited to, data acquired from measuring the user's heart beat; data acquired from measuring the user's eye rotation; data acquired from measuring the user's perspiration; data acquired from measuring the user's respiration; data acquired from measuring the user's oxygen saturation; data acquired from measuring the user's blood pressure; data acquired from measuring the user's skin temperature; data acquired from measuring the user's muscle tension; data acquired from measuring the user's neural activity; data acquired from measuring the user's eye blinking; data acquired from measuring the user's facial expression; data acquired from measuring the user's voice and/or speech; and/or data acquired from measuring the user's hardware interactions.

Once emotional state data associated with a user from the one or more emotional state monitoring systems is received at RECEIVE EMOTIONAL STATE DATA ASSOCIATED WITH A USER FROM THE ONE OR MORE EMOTIONAL STATE MONITORING SYSTEMS OPERATION 313, process flow proceeds to PROVIDE ONE OR MORE ANALYTICS MODULES OPERATION 315.

The analytics modules of PROVIDE ONE OR MORE ANALYTICS MODULES OPERATION 315 are, in one embodiment, "pluggable," e.g., interchangeable, analytics modules to be used with one or more interactive software systems are provided that can be selected, interfaced with, and interchanged, without requiring the redeployment of either the interactive software system or any individual analytics module. In this way, different types of emotional state data can be analyzed and utilized by a single interactive software system or version, or interactive software systems and/or versions, and different analytic algorithms can be interchangeably deployed.

After one or more analytics modules are provided at PROVIDE ONE OR MORE ANALYTICS MODULES OPERATION 315, process flow proceeds to PROVIDE THE EMOTIONAL STATE DATA ASSOCIATED WITH THE USER TO THE ONE OR MORE ANALYTICS MODULES OPERATION 319.

After the emotional state data associated with the user is provided to the one or more analytics modules at PROVIDE THE EMOTIONAL STATE DATA ASSOCIATED WITH THE USER TO THE ONE OR MORE ANALYTICS MODULES OPERATION 319, process flow proceeds to ANALYZE AND/OR COMPARE THE EMOTIONAL STATE DATA ASSOCIATED WITH THE USER TO THE EMOTIONAL STATE THRESHOLD PARAMETER DATA ASSOCIATED WITH THE TYPE OF EMOTIONAL STATE DATA RECEIVED OPERATION 321.

In one embodiment, at ANALYZE AND/OR COMPARE THE EMOTIONAL STATE DATA ASSOCIATED WITH THE USER TO THE EMOTIONAL STATE THRESHOLD PARAMETER DATA ASSOCIATED WITH THE TYPE OF EMOTIONAL STATE DATA RECEIVED OPERATION 321, one or more of the one or more analytics modules of PROVIDE ONE OR MORE ANALYTICS MODULES OPERATION 315 is used to analyze and/or compare the emotional state data received at PROVIDE THE EMOTIONAL STATE DATA ASSOCIATED WITH THE USER TO THE ONE OR MORE ANALYTICS MODULES OPERATION 319 with the associated emotional state threshold parameter data of DEFINE EMOTIONAL STATE THRESHOLD PARAMETER DATA FOR EACH TYPE OF EMOTIONAL STATE DATA OPERATION 311.

After an analytics module analyzes and/or compares the emotional state data associated with the user to the emotional state threshold parameter data associated with the type of emotional state data received at ANALYZE AND/OR COMPARE THE EMOTIONAL STATE DATA ASSOCIATED WITH THE USER TO THE EMOTIONAL STATE THRESHOLD PARAMETER DATA ASSOCIATED WITH THE TYPE OF EMOTIONAL STATE DATA RECEIVED OPERATION 321, process flow proceeds to DETERMINE EMOTIONAL STATE OF USER OPERATION 323.

In one embodiment, at DETERMINE EMOTIONAL STATE OF USER OPERATION 323, an emotional state of a user is determined, based at least in part on the analysis performed at ANALYZE AND/OR COMPARE THE EMOTIONAL STATE DATA ASSOCIATED WITH THE USER TO THE EMOTIONAL STATE THRESHOLD PARAMETER DATA ASSOCIATED WITH THE TYPE OF EMOTIONAL STATE DATA RECEIVED OPERATION 321.

In one embodiment, an emotional state of a user of DETERMINE EMOTIONAL STATE OF USER OPERATION 323 is one or more of the following emotional states: a tense emotional state; a nervous emotional state; a stressed emotional state; an upset emotional state; a frustrated emotional state; a sad emotional state; a depressed emotional state; a bored emotional state; a fatigued emotional state; an alert emotional state; an excited emotional state; an elated emotional state; a happy emotional state; a contented emotional state; a serene emotional state; a relaxed emotional state; and/or a calm emotional state.

After the emotional state of the user is determined at DETERMINE EMOTIONAL STATE OF USER OPERATION 323, process flow proceeds to SELECT ONE OR MORE APPROPRIATE USER EXPERIENCE COMPONENTS TO TRANSFORM THE USER EXPERIENCE PROVIDED THROUGH THE INTERACTIVE SOFTWARE SYSTEM TO A USER EXPERIENCE ADAPTED TO THE DETERMINED EMOTIONAL STATE OF THE USER OPERATION 325.

In various embodiments, the user experience components of SELECT ONE OR MORE APPROPRIATE USER EXPERIENCE COMPONENTS TO TRANSFORM THE USER EXPERIENCE PROVIDED THROUGH THE INTERACTIVE SOFTWARE SYSTEM TO A USER EXPERIENCE ADAPTED TO THE DETERMINED EMOTIONAL STATE OF THE USER OPERATION 325 are selected based on the emotional state of the user. In one embodiment, the interactive software system utilizes algorithms to select user experience components that will optimize the emotional state of a user during and after the user's interaction with the interactive software system. In one embodiment, the interactive software system utilizes algorithms to select user experience components that will maintain the emotional state of a user during and after the user's interaction with the interactive software system.

As a specific example, in a tax preparation service provided by an interactive software system, if an upcoming tax topic will require several questions and interactions to complete, a user experience component or combination of user experience components is selected at SELECT ONE OR MORE APPROPRIATE USER EXPERIENCE COMPONENTS TO TRANSFORM THE USER EXPERIENCE PROVIDED THROUGH THE INTERACTIVE SOFTWARE SYSTEM TO A USER EXPERIENCE ADAPTED TO THE DETERMINED EMOTIONAL STATE OF THE USER OPERATION 325 to adopt different interaction approaches depending on the emotional state of the user. In one embodiment, if the user is happy and upbeat, the topic is addressed in a more matter-of-fact and straightforward manner. If, however, the user is sad or stressed, the user experience component or combination of user experience components is selected at SELECT ONE OR MORE APPROPRIATE USER EXPERIENCE COMPONENTS TO TRANSFORM THE USER EXPERIENCE PROVIDED THROUGH THE INTERACTIVE SOFTWARE SYSTEM TO A USER EXPERIENCE ADAPTED TO THE DETERMINED EMOTIONAL STATE OF THE USER OPERATION 325 to provide a gentler and more upbeat user experience, according to one embodiment. In a tax preparation application, for example, the user experience might provide extra help to the user by selecting user experience components to suggest where the user should go to find each data item needed to complete the application.

For example, in one embodiment, if a user is in a stressed emotional state, a user experience component or combination of user experience components may be selected at SELECT ONE OR MORE APPROPRIATE USER EXPERIENCE COMPONENTS TO TRANSFORM THE USER EXPERIENCE PROVIDED THROUGH THE INTERACTIVE SOFTWARE SYSTEM TO A USER EXPERIENCE ADAPTED TO THE DETERMINED EMOTIONAL STATE OF THE USER OPERATION 325 to provide the user with soothing background colors as part of the user experience. In one embodiment, if the user is in a stressed emotional state, a user experience component or combination of user experience components may be selected at SELECT ONE OR MORE APPROPRIATE USER EXPERIENCE COMPONENTS TO TRANSFORM THE USER EXPERIENCE PROVIDED THROUGH THE INTERACTIVE SOFTWARE SYSTEM TO A USER EXPERIENCE ADAPTED TO THE DETERMINED EMOTIONAL STATE OF THE USER OPERATION 325 to provide the user with soft music as part of the user experience. In one embodiment, if a user is in a stressed emotional state, a user experience component or combination of user experience components is selected at SELECT ONE OR MORE APPROPRIATE USER EXPERIENCE COMPONENTS TO TRANSFORM THE USER EXPERIENCE PROVIDED THROUGH THE INTERACTIVE SOFTWARE SYSTEM TO A USER EXPERIENCE ADAPTED TO THE DETERMINED EMOTIONAL STATE OF THE USER OPERATION 325 to provide the user with additional assistance as part of the user experience.

In one embodiment, a user experience component or combination of user experience components will be selected at SELECT ONE OR MORE APPROPRIATE USER EXPERIENCE COMPONENTS TO TRANSFORM THE USER EXPERIENCE PROVIDED THROUGH THE INTERACTIVE SOFTWARE SYSTEM TO A USER EXPERIENCE ADAPTED TO THE DETERMINED EMOTIONAL STATE OF THE USER OPERATION 325 to provide the user with a user experience that presents any questions and/or suggestions in a specific order, based on the user's emotional state. In one embodiment, for example, if the user is determined to be in a stressed emotional state, a user experience component or combination of user experience components will be selected at SELECT ONE OR MORE APPROPRIATE USER EXPERIENCE COMPONENTS TO TRANSFORM THE USER EXPERIENCE PROVIDED THROUGH THE INTERACTIVE SOFTWARE SYSTEM TO A USER EXPERIENCE ADAPTED TO THE DETERMINED EMOTIONAL STATE OF THE USER OPERATION 325 to provide the user with a user experience that avoids any difficult/unpleasant questions and/or suggestions. In one embodiment, if the user is determined to be in a stressed emotional state, a user experience component or combination of user experience components will be selected at SELECT ONE OR MORE APPROPRIATE USER EXPERIENCE COMPONENTS TO TRANSFORM THE USER EXPERIENCE PROVIDED THROUGH THE INTERACTIVE SOFTWARE SYSTEM TO A USER EXPERIENCE ADAPTED TO THE DETERMINED EMOTIONAL STATE OF THE USER OPERATION 325 to provide the user with a user experience that avoids any questions and/or suggestions requiring the user to find and/or provide data to the interactive software system.

According to one embodiment, a user experience component or combination of user experience components is selected at SELECT ONE OR MORE APPROPRIATE USER EXPERIENCE COMPONENTS TO TRANSFORM THE USER EXPERIENCE PROVIDED THROUGH THE INTERACTIVE SOFTWARE SYSTEM TO A USER EXPERIENCE ADAPTED TO THE DETERMINED EMOTIONAL STATE OF THE USER OPERATION 325 to provide the user with an alert; insert human resource assistance; and/or any other form of user assistance when the user is, for example, in a nervous, frustrated, stressed, and/or upset emotional state. If the user is in, for example, a nervous, frustrated, stressed, and/or upset emotional state, a user experience component or combination of user experience components is selected at SELECT ONE OR MORE APPROPRIATE USER EXPERIENCE COMPONENTS TO TRANSFORM THE USER EXPERIENCE PROVIDED THROUGH THE INTERACTIVE SOFTWARE SYSTEM TO A USER EXPERIENCE ADAPTED TO THE DETERMINED EMOTIONAL STATE OF THE USER OPERATION 325 to provide an alert to the user for a customer service professional and/or for a system administrator, according to one embodiment.

Furthermore, in various embodiments, the selection of a user experience component or combination of user experience components at SELECT ONE OR MORE APPROPRIATE USER EXPERIENCE COMPONENTS TO TRANSFORM THE USER EXPERIENCE PROVIDED THROUGH THE INTERACTIVE SOFTWARE SYSTEM TO A USER EXPERIENCE ADAPTED TO THE DETERMINED EMOTIONAL STATE OF THE USER OPERATION 325 depends at least in part on whether the user is the end customer or a human service provider for the customer. For example, if the user is an accountant interacting with the interactive software system based on the accountant's client's behalf, the appropriate user experience components may be selected to adapt the user experience to the user's status as a human service provider.

In various embodiments, the experience level of the user is taken into consideration when selecting a user experience component or combination of user experience components at SELECT ONE OR MORE APPROPRIATE USER EXPERIENCE COMPONENTS TO TRANSFORM THE USER EXPERIENCE PROVIDED THROUGH THE INTERACTIVE SOFTWARE SYSTEM TO A USER EXPERIENCE ADAPTED TO THE DETERMINED EMOTIONAL STATE OF THE USER OPERATION 325. For example, in a tax preparation application, if the user is an accountant, it may be assumed that the user has a higher level of proficiency in tax preparation than that of a non-accountant user. As a result, if the user is frustrated and the user is an accountant, the underlying cause of the frustration may be different than the cause of frustration for a frustrated non-accountant user. Therefore, in one embodiment, a user experience component or combination of user experience components selected at SELECT ONE OR MORE APPROPRIATE USER EXPERIENCE COMPONENTS TO TRANSFORM THE USER EXPERIENCE PROVIDED THROUGH THE INTERACTIVE SOFTWARE SYSTEM TO A USER EXPERIENCE ADAPTED TO THE DETERMINED EMOTIONAL STATE OF THE USER OPERATION 325 for a frustrated accountant user is different than those selected for a frustrated non-accountant user.

Thus, at SELECT ONE OR MORE APPROPRIATE USER EXPERIENCE COMPONENTS TO TRANSFORM THE USER EXPERIENCE PROVIDED THROUGH THE INTERACTIVE SOFTWARE SYSTEM TO A USER EXPERIENCE ADAPTED TO THE DETERMINED EMOTIONAL STATE OF THE USER OPERATION 325, the interactive software system can adapt to the user's profession and/or level of experience when selecting a user experience component or combination of user experience components. In one embodiment, if the user is an accountant, the interactive software system may assume that the user has certain knowledge and/or a preferred approach for specific tasks than users who are not accountants. Based on this assumption, a user experience component or combination of user experience components may then be selected at SELECT ONE OR MORE APPROPRIATE USER EXPERIENCE COMPONENTS TO TRANSFORM THE USER EXPERIENCE PROVIDED THROUGH THE INTERACTIVE SOFTWARE SYSTEM TO A USER EXPERIENCE ADAPTED TO THE DETERMINED EMOTIONAL STATE OF THE USER OPERATION 325 to provide an appropriate user experience.

As one example, an interactive software system that provides accounting services for small businesses may select a user experience component or combination of user experience components at SELECT ONE OR MORE APPROPRIATE USER EXPERIENCE COMPONENTS TO TRANSFORM THE USER EXPERIENCE PROVIDED THROUGH THE INTERACTIVE SOFTWARE SYSTEM TO A USER EXPERIENCE ADAPTED TO THE DETERMINED EMOTIONAL STATE OF THE USER OPERATION 325 based on whether there are a significant number of overdue invoices or whether the business's overall cash flow has been negative for some length of time. Additionally, because an accountant user may be less emotionally involved in overdue invoices or negative cash flow than the small business owner for whom the accountant is providing services, the user experience component or combination of user experience components selected at SELECT ONE OR MORE APPROPRIATE USER EXPERIENCE COMPONENTS TO TRANSFORM THE USER EXPERIENCE PROVIDED THROUGH THE INTERACTIVE SOFTWARE SYSTEM TO A USER EXPERIENCE ADAPTED TO THE DETERMINED EMOTIONAL STATE OF THE USER OPERATION 325 for an accountant user may differ than those selected for an owner user. Furthermore, depending on the emotional state of the user and/or on whether the user is an accountant or owner, the user experience component or combination of user experience components could be selected at SELECT ONE OR MORE APPROPRIATE USER EXPERIENCE COMPONENTS TO TRANSFORM THE USER EXPERIENCE PROVIDED THROUGH THE INTERACTIVE SOFTWARE SYSTEM TO A USER EXPERIENCE ADAPTED TO THE DETERMINED EMOTIONAL STATE OF THE USER OPERATION 325 to suggest that the interactive software system engage in a cash flow analysis based on different strategies for tax payments or accounts receivables.

Similarly, an interactive software system that provides financial management services may, in one embodiment, consider the net worth of the user when selecting a user experience component or combination of user experience components at SELECT ONE OR MORE APPROPRIATE USER EXPERIENCE COMPONENTS TO TRANSFORM THE USER EXPERIENCE PROVIDED THROUGH THE INTERACTIVE SOFTWARE SYSTEM TO A USER EXPERIENCE ADAPTED TO THE DETERMINED EMOTIONAL STATE OF THE USER OPERATION 325. If the user's net worth has been steadily increasing over some period of time and the user has been consistently interacting with the interactive software system in a happy emotional state, the interactive software system may select a user experience component or combination of user experience components at SELECT ONE OR MORE APPROPRIATE USER EXPERIENCE COMPONENTS TO TRANSFORM THE USER EXPERIENCE PROVIDED THROUGH THE INTERACTIVE SOFTWARE SYSTEM TO A USER EXPERIENCE ADAPTED TO THE DETERMINED EMOTIONAL STATE OF THE USER OPERATION 325 to suggest that the user contribute the maximum amount of money possible to his or her 401K, put money into an IRA, and take an expensive vacation. In one embodiment, a user experience component or combination of user experience components may be adapted during the user's interaction with the interactive software system as the user's emotional state may change during the interaction. Thus, the selected user experience component or combination of user experience components can be selected at SELECT ONE OR MORE APPROPRIATE USER EXPERIENCE COMPONENTS TO TRANSFORM THE USER EXPERIENCE PROVIDED THROUGH THE INTERACTIVE SOFTWARE SYSTEM TO A USER EXPERIENCE ADAPTED TO THE DETERMINED EMOTIONAL STATE OF THE USER OPERATION 325 to dynamically adapt the user experience in response to a user's changing emotional state.

In one embodiment, the interactive software system utilizes baseline emotional state data (from the user's past emotional state data and/or some general population's emotional state data) to predict a user's emotional state. For example, in one embodiment, the interactive software system predicts that a user interacting with the interactive software system on a Monday morning is in a more positive emotional state than a user interacting with the interactive software system on a Friday afternoon or on a weekend.

By selecting an appropriate user experience component or combination of user experience components at SELECT ONE OR MORE APPROPRIATE USER EXPERIENCE COMPONENTS TO TRANSFORM THE USER EXPERIENCE PROVIDED THROUGH THE INTERACTIVE SOFTWARE SYSTEM TO A USER EXPERIENCE ADAPTED TO THE DETERMINED EMOTIONAL STATE OF THE USER OPERATION 325 to present a customized user experience to a user, the present disclosure allows for significant improvement to the technical fields of user experience, customer service, data collection, and data processing. Indeed, by minimizing and potentially eliminating the presentation of an irrelevant user experience to a user, embodiments of the present disclosure use fewer human resources like time and energy by not selecting an irrelevant or even frustrating a user experience component or combination of user experience components. Similarly, by selecting an appropriate a user experience component or combination of user experience components at SELECT ONE OR MORE APPROPRIATE USER EXPERIENCE COMPONENTS TO TRANSFORM THE USER EXPERIENCE PROVIDED THROUGH THE INTERACTIVE SOFTWARE SYSTEM TO A USER EXPERIENCE ADAPTED TO THE DETERMINED EMOTIONAL STATE OF THE USER OPERATION 325 to provide a customized user experience, embodiments of the present disclosure actually improve the efficiency of the user experience by presenting a user experience that makes a user's interaction with an interactive software system easier and less stressful.

Furthermore, by allowing for more relevant interactions between a user and an interactive software system, embodiments of the present disclosure require fewer processing cycles and less communications bandwidth. As a result, embodiments of the present disclosure allow for improved processor performance, more efficient use of memory access and data storage capabilities, reduced communication channel bandwidth utilization, faster communications connections, and improved user efficiency. Consequently, computing and software systems are transformed into faster and more operationally efficient devices and systems by implementing and/or providing the embodiments of the present disclosure. Therefore, implementation of embodiments of the present disclosure amounts to significantly more than an abstract idea and also provides several improvements to multiple technical fields.

After one or more appropriate user experience components are selected to transform the user experience provided through the interactive software system to a user experience adapted to the determined emotional state of the user at SELECT ONE OR MORE APPROPRIATE USER EXPERIENCE COMPONENTS TO TRANSFORM THE USER EXPERIENCE PROVIDED THROUGH THE INTERACTIVE SOFTWARE SYSTEM TO A USER EXPERIENCE ADAPTED TO THE DETERMINED EMOTIONAL STATE OF THE USER OPERATION 325, process flow proceeds to PRESENT USER EXPERIENCE ADAPTED TO THE DETERMINED EMOTIONAL STATE OF THE USER TO THE USER OPERATION 327.

In one embodiment, at PRESENT USER EXPERIENCE ADAPTED TO THE DETERMINED EMOTIONAL STATE OF THE USER TO THE USER OPERATION 327, the user experience is presented to the user on a user computing system, such as any of the computing systems discussed herein, and/or as known in the art at the time of filing, and/or as developed after the time of filing.

In one embodiment, once the user experience adapted to the determined emotional state of the user is presented to the user at PRESENT USER EXPERIENCE ADAPTED TO THE DETERMINED EMOTIONAL STATE OF THE USER TO THE USER OPERATION 327, process flow proceeds to EXIT OPERATION 329.

In one embodiment, at EXIT OPERATION 329, process 300 for using emotional state data to tailor the user experience of an interactive software system is exited to await new data.

Implementations of embodiments of process 300 for using emotional state data to tailor the user experience of an interactive software system significantly improve the technical fields of software systems, user experience, customer service, data collection, and data processing. Therefore, the various described embodiments of the disclosure and their associated benefits amount to significantly more than an abstract idea. In particular, by individualizing or personalizing the user experience, an interactive software system may be able to provide a more useful service to the user. For example, in one embodiment, an interactive software system providing a tax return preparation service may be able to gather more complete information from the user and provide a more thorough and customized analysis of potential tax return benefits for the user, all without adversely affecting the user's emotional state.

In addition, as noted above, by minimizing, or potentially eliminating, the processing and presentation of an inappropriate user experience to a user, implementation of embodiments of the present disclosure allows for significant improvement to the field of data collection and data processing. As one illustrative example, by minimizing, or potentially eliminating, the processing and presentation of an inappropriate user experience to a user, implementation of embodiments of the present disclosure allows for relevant data collection using fewer processing cycles and less communications bandwidth. Furthermore, when a user is presented with an inappropriate user experience, the user is much more likely to abandon the interactive software system altogether, thereby wasting all the processing cycles and communications bandwidth already invested in the user. Thus, by processing and presenting an appropriate user experience to a user, a user is less likely to abandon the interactive software system. As a result, embodiments of the present disclosure allow for improved processor performance, more efficient use of memory access and data storage capabilities, reduced communication channel bandwidth utilization, and faster communications connections. Consequently, computing and communication systems implementing and/or providing the embodiments of the present disclosure are transformed into faster and more operationally efficient devices and systems.

As a result of providing a selected user experience component or combination of selected user experience components, the static and inflexible user experiences of traditional interactive software systems are replaced with efficient and dynamically modifiable user experiences, thereby improving the technical fields of customer service, user experience, and software application modification and update.

The present invention has been described in particular detail with respect to specific possible embodiments. Those of skill in the art will appreciate that the invention may be practiced in other embodiments. For example, the nomenclature used for components, capitalization of component designations and terms, the attributes, data structures, or any other programming or structural aspect is not significant, mandatory, or limiting, and the mechanisms that implement the invention or its features can have various different names, formats, and/or protocols. Further, the system and/or functionality of the invention may be implemented via various combinations of software and hardware, as described, or entirely in hardware elements. Also, particular divisions of functionality between the various components described herein are merely exemplary, and not mandatory or significant. Consequently, functions performed by a single component may, in other embodiments, be performed by multiple components, and functions performed by multiple components may, in other embodiments, be performed by a single component.

Some portions of the above description present the features of the present invention in terms of algorithms and symbolic representations of operations, or algorithm-like representations, of operations on information/data. These algorithmic and/or algorithm-like descriptions and representations are the means used by those of skill in the art to most effectively and efficiently convey the substance of their work to others of skill in the art. These operations, while described functionally or logically, are understood to be implemented by computer programs and/or computing systems. Furthermore, it has also proven convenient at times to refer to these arrangements of operations as steps or modules or by functional names, without loss of generality.

Unless specifically stated otherwise, as would be apparent from the above discussion, it is appreciated that throughout the above description, discussions utilizing terms such as "accessing," "analyzing," "associating," "aggregating," "collecting," "creating," "comparing," "defining," "determining," "generating," "identifying," "initiating," "obtaining," "providing," "processing," "presenting," "receiving," "storing," "searching," "selecting," "transferring," etc., refer to the action and processes of a computing system or similar electronic device that manipulates and operates on data represented as physical (electronic) quantities within the computing system memories, resisters, caches or other information storage, transmission or display devices.

Certain aspects of the present invention include process steps or operations and instructions described herein in an algorithmic and/or algorithmic-like form. It should be noted that the process steps and/or operations and instructions of the present invention can be embodied in software, firmware, and/or hardware, and when embodied in software, can be downloaded to reside on and be operated from different platforms used by real-time network operating systems.

The present invention also relates to an apparatus or system for performing the operations described herein. This apparatus or system may be specifically constructed for the required purposes by a computer program stored via a computer program product as defined herein that can be accessed by a computing system or other device to transform the computing system or other device into a specifically and specially programmed computing system or other device.

Those of skill in the art will readily recognize that the algorithms and operations presented herein are not inherently related to any particular computing system, computer architecture, computer or industry standard, or any other specific apparatus. It may prove convenient and/or efficient to construct or transform one or more specialized apparatuses to perform the required operations described herein. The required structure for a variety of these systems will be apparent to those of skill in the art, along with equivalent variations. In addition, the present invention is not described with reference to any particular programming language and it is appreciated that a variety of programming languages may be used to implement the teachings of the present invention as described herein, and any references to a specific language or languages are provided for illustrative purposes only and for enablement of the contemplated best mode of the invention at the time of filing.

The present invention is well suited to a wide variety of computer network systems operating over numerous topologies. Within this field, the configuration and management of large networks comprise storage devices and computers that are communicatively coupled to similar and/or dissimilar computers and storage devices over a private network, a LAN, a WAN, a private network, or a public network, such as the Internet.

It should also be noted that the language used in the specification has been principally selected for readability, clarity, and instructional purposes, and may not have been selected to delineate or circumscribe the inventive subject matter. Accordingly, the disclosure of the present invention is intended to be illustrative, but not limiting, of the scope of the invention, which is set forth in the claims below.

In addition, the operations shown in the FIG.s are identified using a particular nomenclature for ease of description and understanding, but other nomenclature is often used in the art to identify equivalent operations.

As discussed above, using the above embodiments, with little or no modification and/or input, there is considerable flexibility, adaptability, and opportunity for customization to meet the specific needs of various users under numerous circumstances. In the discussion above, certain aspects of one embodiment include process steps and/or operations and/or instructions described herein for illustrative purposes in a particular order and/or grouping. However, the particular order and/or grouping shown and discussed herein are illustrative only and not limiting. Those of skill in the art will recognize that other orders and/or grouping of the process steps and/or operations and/or instructions are possible and, in some embodiments, one or more of the process steps and/or operations and/or instructions discussed above can be combined and/or deleted. In addition, portions of one or more of the process steps and/or operations and/or instructions can be re-grouped as portions of one or more other of the process steps and/or operations and/or instructions discussed herein. Consequently, the particular order and/or grouping of the process steps and/or operations and/or instructions discussed herein do not limit the scope of the invention as claimed below.

Therefore, numerous variations, whether explicitly provided for by the specification or implied by the specification or not, may be implemented by one of skill in the art in view of this disclosure.

What is claimed is:

1. A method for using emotional state data to tailor the user experience of an interactive software system comprising:

providing an interactive software system;

defining one or more user experience components, the one or more user experience components capable of combination to provide a user experience through the interactive software system, the defined user experience components including each of lengths of descriptions provided to a user and images provided to the user;

generating user experience component data, the user experience component data representing the defined one or more user experience components;

storing the user experience component data in a partitioned user experience data section of a memory device and/or system;

defining emotional state data to be obtained and analyzed;

defining emotional state threshold parameter data for each defined type of emotional state data to be obtained and analyzed;

generating emotional state threshold parameter data representing the defined emotional state threshold parameters for each defined type of emotional state data to be obtained and analyzed;

storing the emotional state threshold parameter data in a partitioned emotional state threshold parameter data section of a memory device and/or system;

providing one or more analytics modules, the one or more analytics modules implementing one or more user emotional state adaptation algorithms;

providing the one or more analytics modules access to the emotional state threshold parameter data in the partitioned emotional state threshold parameter data section of the memory device and/or system;

obtaining emotional state data associated with a user and also obtaining financial information reflecting a response to a query, the response indicating that the user is unable to accomplish a desired task associated with the query due to the user's financial condition, the obtained emotional state data being one or more of the defined one or more types of emotional state data, the emotional state data at least including data acquired by measuring muscle tension of the user;

providing the obtained emotional state data to the one or more analytics modules;

analyzing the obtained emotional state data, the emotional state parameter data associated with the one or more types of obtained emotional state data, and the financial information reflecting the response to the query;

based, at least in part, on the analysis of the obtained emotional state data, the emotional state parameter data associated with the one or more types of obtained emotional state data, and the financial information reflecting the response to the query, predicting a future emotional state of the user;

based, at least in part, on the predicted future emotional state of the user, selecting a portion of the user experience component data, the selected portion of the user experience component data representing one or more selected user experience components of the defined one or more user experience components;

using the portion of the user experience component data representing one or more selected user experience components of the defined one or more user experience components to transform a user experience provided through the interactive software system into a user experience adapted to the predicted future emotional state of the user; and providing the user experience adapted to the predicted future emotional state of the user to the user.

2. The method for using emotional state data to tailor the user experience of an interactive software system of claim 1, wherein the interactive software system is selected from the group of interactive software systems consisting of:

a computing system implemented tax preparation software system;
a network accessed tax preparation software system;
a web-based tax preparation software system;
a cloud-based tax preparation software system;
a computing system implemented business management software system;
a network accessed business management software system;
a web-based business management software system;
a cloud-based business management software system;
a computing system implemented accounting software system;
a network accessed accounting software system;
a web-based accounting software system;
a cloud-based accounting software system;
a computing system implemented financial management system;
a network accessed financial management system;
a web-based financial management system; and
a cloud-based financial management system.

3. The method for using emotional state data to tailor the user experience of an interactive software system of claim 1, wherein the user experience is presented to the user via at least one computing system selected from the group of computing systems consisting of:

a server computing system;
a workstation;
a desktop computing system;
a database system or storage cluster;
a virtual asset;
a switching system;
a router;
a hardware system;
a communications system;
a proxy system;
a gateway system;
a firewall system; and
a load balancing system.

4. The method for using emotional state data to tailor the user experience of an interactive software system of claim 1, wherein the user experience components include at least one user experience component selected from the group of user experience components consisting of:

a sequence with which interview questions are presented to the user;
content or topics of the interview questions that are presented to the user;
font sizes used while presenting information to the user;
themes presented to the user;
types of icons displayed to the user;
types of interface formats presented to the user;
interface displays presented to the user;
assistance resources listed and/or recommended to the user;
user recommendations presented to the user;
backgrounds presented to the user;
background audio presented to the user;
avatars and/or icons presented to the user;
highlighting mechanisms used and highlighted components presented to the user;
support mechanisms presented to the user; and
supplemental actions and recommendations presented to the user.

5. The method for using emotional state data to tailor the user experience of an interactive software system of claim 1, wherein the emotional state data includes at least one of the emotional state data selected from the group of emotional state data consisting of:
data acquired from the user's own characterization of his or her emotional state;
data acquired from historical user data;
data acquired from a segment of users having characteristics comparable to the user;
data acquired from measuring the user's heart beat;
data acquired from measuring the user's eye rotation;
data acquired from measuring the user's perspiration;
data acquired from measuring the user's respiration;
data acquired from measuring the user's oxygen saturation;
data acquired from measuring the user's blood pressure
data acquired from measuring the user's skin temperature;
data acquired from measuring the user's neural activity;
data acquired from measuring the user's eye blinking;
data acquired from measuring the user's facial expression;
data acquired from measuring the user's voice and/or speech; and
data acquired from measuring the user's interactions with hardware associated with an interactive software system.

6. The method for using emotional state data to tailor the user experience of an interactive software system of claim 1, wherein the emotional state threshold parameters for each defined type of emotional state data to be obtained and analyzed are defined based on emotional state data associated with a general population.

7. The method for using emotional state data to tailor the user experience of an interactive software system of claim 6, wherein the emotional state threshold parameters for each defined type of emotional state data to be obtained and analyzed include at least one of emotional state threshold parameter selected from the group of emotional state threshold parameters consisting of:
a heart rate emotional state threshold parameter associated with a user's heart beat;
a heart rate variability level emotional state threshold parameter associated with a user's heart beat;
a scan path emotional state threshold parameter associated with a user's eye rotation;
a fixation period emotional state threshold parameter associated with a user's eye rotation;
a skin conductance level emotional state threshold parameter associated with a user's perspiration;
a respiration rate emotional state threshold parameter associated with a user's respiration;
an oxygen saturation level emotional state threshold parameter associated with a user's oxygen saturation;
a blood pressure level emotional state threshold parameter associated with a user's blood pressure;
a skin temperature emotional state threshold parameter associated with a user's skin temperature;
a muscle tension level emotional state threshold parameter associated with a user's muscle tension;
a neural activity level emotional state threshold parameter associated with a user's neural activity;
an eye blink rate emotional state threshold parameter associated with a user's eye blinking;
a facial muscle movement emotional state threshold parameter associated with a user's facial expression;
an acoustic characteristics emotional state threshold parameter associated with a user's voice and/or speech;
a contact pressure emotional state threshold parameter associated with the user's interactions with hardware associated with an interactive software system; and
a contact rate emotional state threshold parameter associated with the user's interactions with hardware associated with an interactive software system.

8. The method for using emotional state data to tailor the user experience of an interactive software system of claim 1, wherein the emotional state threshold parameters for each defined type of emotional state data to be obtained and analyzed are customized based on emotional state profile data associated with the specific user.

9. The method for using emotional state data to tailor the user experience of an interactive software system of claim 8, wherein the customized emotional state threshold parameters include at least one of the customized emotional state threshold parameter selected from the group of customized emotional state threshold parameters consisting of:
a heart rate emotional state threshold parameter associated with the user's heart beat
a heart rate variability level emotional state threshold parameter associated with the user's heart beat;
a scan path emotional state threshold parameter associated with the user's eye rotation;
a fixation period emotional state threshold parameter associated with the user's eye rotation;
a skin conductance level emotional state threshold parameter associated with the user's perspiration;
a respiration rate emotional state threshold parameter associated with the user's respiration;
an oxygen saturation level emotional state threshold parameter associated with the user's oxygen saturation;
a blood pressure level emotional state threshold parameter associated with the user's blood pressure;
a skin temperature emotional state threshold parameter associated with the user's skin temperature;
a muscle tension level emotional state threshold parameter associated with the user's muscle tension;
a neural activity level emotional state threshold parameter associated with the user's neural activity;
an eye blink rate emotional state threshold parameter associated with the user's eye blinking;
a facial muscle movement emotional state threshold parameter associated with the user's facial expression;
an acoustic characteristics emotional state threshold parameter associated with the user's voice and/or speech;

a contact pressure emotional state threshold parameter associated with the user's interactions with hardware associated with an interactive software system; and a contact rate emotional state threshold parameter associated with the user's interactions with hardware associated with an interactive software system.

10. The method for using emotional state data to tailor the user experience of an interactive software system of claim 1, wherein at least one of the one or more analytics modules is an interchangeable analytics module.

11. The method for using emotional state data to tailor the user experience of an interactive software system of claim 1, wherein an emotional state of the user includes at least one of the emotional states selected from the group of emotional states consisting of:

a happy emotional state or happiness;
a sad emotional state or sadness;
a surprised emotional state or surprise;
a fearful emotional state or fear;
a disgusted emotional state or disgust;
an angry emotional state or anger;
a tense emotional state;
a nervous emotional state;
a stressed emotional state;
an upset emotional state;
a frustrated emotional state;
a depressed emotional state;
a bored emotional state;
a fatigued emotional state;
an alert emotional state;
an excited emotional state;
an elated emotional state;
a happy emotional state;
a contented emotional state;
a serene emotional state;
a relaxed emotional state; and
a calm emotional state.

12. The method for using emotional state data to tailor the user experience of an interactive software system of claim 1, wherein transforming the user experience provided through the interactive software system into a user experience adapted to the predicted future emotional state of the user includes adding one or more user experience components to the user experience.

13. The method for using emotional state data to tailor the user experience of an interactive software system of claim 1, wherein transforming the user experience provided through the interactive software system into a user experience adapted to the predicted future emotional state of the user includes removing one or more user experience components from the user experience.

14. The method for using emotional state data to tailor the user experience of an interactive software system of claim 1, wherein the user experience adapted to the predicted future emotional state of the user is provided to the user via a user display screen displayed on a user computing system accessible by the user.

15. The method for using emotional state data to tailor the user experience of an interactive software system of claim 1, wherein the emotional state data associated with a user is obtained on a periodic basis and the user experience adapted to the predicted future emotional state of the user is modified and provided to the user on a periodic basis.

16. A system for providing an interactive software system with a user experience adapted to a user's emotional state comprising:

an interactive software system;

a partitioned user experience data section of a memory device and/or system, the user experience data section including user experience component data, the user experience component data representing one or more user experience components, the one or more user experience components capable of combination to provide a user experience through the interactive software system, the user experience components including each of lengths of descriptions provided to a user and images provided to the user;

a partitioned emotional state data section of a memory device and/or system, the emotional state data section including emotional state data to be obtained and analyzed, the emotional state data having been defined;

a partitioned emotional state threshold parameter data section of a memory device and/or system, the emotional state threshold parameter data section including emotional state threshold parameter data for each defined type of emotional state data to be obtained and analyzed; the emotional state threshold parameter having been defined;

one or more analytics modules, the one or more analytics modules implementing one or more user emotional state adaptation algorithms, the one or more analytics modules having access to the emotional state threshold parameter data;

an emotional state data receiving module, the emotional state data receiving module obtaining emotional state data associated with a user and also obtaining financial information reflecting a response to a query, the response indicating that the user is unable to accomplish a desired task associated with the query due to the user's financial condition, the obtained emotional state data being one or more of the defined one or more types of emotional state data, the emotional state data at least including data acquired by measuring muscle tension of the user, the emotional state data receiving module providing the obtained emotional state data to the one or more analytics modules, the one or more analytics modules analyzing the obtained emotional state data, the emotional state parameter data associated with the one or more types of obtained emotional state data, and financial information reflecting a response to a query;

an emotional state determining module, the emotional state determining module predicting a future emotional state of the user based, at least in part, on the analysis of the obtained emotional state data, the emotional state parameter data associated with the one or more types of obtained emotional state data and the financial information reflecting a response to a query;

a selecting module, the selecting module selecting a portion of the user experience component data, the selected portion of the user experience component data representing one or more selected user experience components of the defined one or more user experience components, the selection based, at least in part, on the predicted future emotional state of the user;

a user experience transformation module, the user experience transformation module using the portion of the user experience component data representing one or more selected user experience components of the defined one or more user experience components to transform a user experience provided through the interactive software system into a user experience adapted to the predicted future emotional state of the user; and a transfer module, the transfer module providing data representing the user experience adapted to the predicted future emotional state of the user to the user.

17. The system for providing an interactive software system with a user experience adapted to a user's emotional state of claim 16, wherein the interactive software system is selected from the group of interactive software systems consisting of:
- a computing system implemented tax preparation software system;
- a network accessed tax preparation software system;
- a web-based tax preparation software system;
- a cloud-based tax preparation software system;
- a computing system implemented business management software system;
- a network accessed business management software system;
- a web-based business management software system;
- a cloud-based business management software system;
- a computing system implemented accounting software system;
- a network accessed accounting software system;
- a web-based accounting software system;
- a cloud-based accounting software system;
- a computing system implemented financial management system;
- a network accessed financial management system;
- a web-based financial management system; and
- a cloud-based financial management system.

18. The system for providing an interactive software system with a user experience adapted to a user's emotional state of claim 16, wherein the user experience is presented to the user via at least one computing system selected from the group of computing systems consisting of:
- a server computing system;
- a workstation;
- a desktop computing system;
- a mobile computing system;
- a database system or storage cluster;
- a virtual asset;
- a switching system;
- a router;
- a hardware system;
- a communications system;
- a proxy system;
- a gateway system;
- a firewall system; and
- a load balancing system.

19. The system for providing an interactive software system with a user experience adapted to a user's emotional state of claim 16, wherein the user experience components include at least one user experience component selected from the group of user experience components consisting of:
- a sequence with which interview questions are presented to the user;
- content or topics of the interview questions that are presented to the user;
- font sizes used while presenting information to the user;
- themes presented to the user;
- types of icons displayed to the user;
- types of interface formats presented to the user;
- interface displays presented to the user;
- assistance resources listed and/or recommended to the user;
- user recommendations presented to the user;
- backgrounds presented to the user;
- background audio presented to the user;
- avatars and/or icons presented to the user;
- highlighting mechanisms used and highlighted components presented to the user;
- support mechanisms presented to the user; and
- supplemental actions and recommendations presented to the user.

20. The system for providing an interactive software system with a user experience adapted to a user's emotional state of claim 16, wherein the emotional state data includes at least one of the emotional state data selected from the group of emotional state data consisting of:
- data acquired from the user's own characterization of his or her emotional state;
- data acquired from historical user data;
- data acquired from a segment of users having characteristics comparable to the user;
- data acquired from measuring the user's heart beat;
- data acquired from measuring the user's eye rotation;
- data acquired from measuring the user's perspiration;
- data acquired from measuring the user's respiration;
- data acquired from measuring the user's oxygen saturation;
- data acquired from measuring the user's blood pressure
- data acquired from measuring the user's skin temperature;
- data acquired from measuring the user's neural activity;
- data acquired from measuring the user's eye blinking;
- data acquired from measuring the user's facial expression;
- data acquired from measuring the user's voice and/or speech; and
- data acquired from measuring the user's interactions with hardware associated with an interactive software system.

21. The system for providing an interactive software system with a user experience adapted to a user's emotional state of claim 16, wherein the emotional state threshold parameters for each defined type of emotional state data to be obtained and analyzed are defined based on emotional state data associated with a general population.

22. The system for providing an interactive software system with a user experience adapted to a user's emotional state of claim 21, wherein the emotional state threshold parameters for each defined type of emotional state data to be obtained and analyzed include at least one of emotional state threshold parameter selected from the group of emotional state threshold parameters consisting of:
- a heart rate emotional state threshold parameter associated with a user's heart beat
- a heart rate variability level emotional state threshold parameter associated with a user's heart beat;
- a scan path emotional state threshold parameter associated with a user's eye rotation;
- a fixation period emotional state threshold parameter associated with a user's eye rotation;
- a skin conductance level emotional state threshold parameter associated with a user's perspiration;
- a respiration rate emotional state threshold parameter associated with a user's respiration;
- an oxygen saturation level emotional state threshold parameter associated with a user's oxygen saturation;
- a blood pressure level emotional state threshold parameter associated with a user's blood pressure;

a skin temperature emotional state threshold parameter associated with a user's skin temperature;
a muscle tension level emotional state threshold parameter associated with a user's muscle tension;
a neural activity level emotional state threshold parameter associated with a user's neural activity;
an eye blink rate emotional state threshold parameter associated with a user's eye blinking;
a facial muscle movement emotional state threshold parameter associated with a user's facial expression;
an acoustic characteristics emotional state threshold parameter associated with a user's voice and/or speech;
a contact pressure emotional state threshold parameter associated with the user's interactions with hardware associated with an interactive software system; and
a contact rate emotional state threshold parameter associated with the user's interactions with hardware associated with an interactive software system.

23. The system for providing an interactive software system with a user experience adapted to a user's emotional state of claim 16, wherein the emotional state threshold parameters for each defined type of emotional state data to be obtained and analyzed are customized based on emotional state profile data associated with the specific user.

24. The system for providing an interactive software system with a user experience adapted to a user's emotional state of claim 23, wherein the customized emotional state threshold parameters include at least one of the customized emotional state threshold parameter selected from the group of customized emotional state threshold parameters consisting of:
   a heart rate emotional state threshold parameter associated with the user's heart beat
   a heart rate variability level emotional state threshold parameter associated with the user's heart beat;
   a scan path emotional state threshold parameter associated with the user's eye rotation;
   a fixation period emotional state threshold parameter associated with the user's eye rotation;
   a skin conductance level emotional state threshold parameter associated with the user's perspiration;
   a respiration rate emotional state threshold parameter associated with the user's respiration;
   an oxygen saturation level emotional state threshold parameter associated with the user's oxygen saturation;
   a blood pressure level emotional state threshold parameter associated with the user's blood pressure;
   a skin temperature emotional state threshold parameter associated with the user's skin temperature;
   a muscle tension level emotional state threshold parameter associated with the user's muscle tension;
   a neural activity level emotional state threshold parameter associated with the user's neural activity;
   an eye blink rate emotional state threshold parameter associated with the user's eye blinking;
   a facial muscle movement emotional state threshold parameter associated with the user's facial expression;
   an acoustic characteristics emotional state threshold parameter associated with the user's voice and/or speech;
   a contact pressure emotional state threshold parameter associated with the user's interactions with hardware associated with an interactive software system; and
   a contact rate emotional state threshold parameter associated with the user's interactions with hardware associated with an interactive software system.

25. The system for providing an interactive software system with a user experience adapted to a user's emotional state of claim 16, wherein at least one of the one or more analytics modules is an interchangeable analytics module.

26. The system for providing an interactive software system with a user experience adapted to a user's emotional state of claim 16, wherein an emotional state of the user includes at least one of the emotional states selected from the group of emotional states consisting of:
   a happy emotional state or happiness;
   a sad emotional state or sadness;
   a surprised emotional state or surprise;
   a fearful emotional state or fear;
   a disgusted emotional state or disgust;
   an angry emotional state or anger;
   a tense emotional state;
   a nervous emotional state;
   a stressed emotional state;
   an upset emotional state;
   a frustrated emotional state;
   a depressed emotional state;
   a bored emotional state;
   a fatigued emotional state;
   an alert emotional state;
   an excited emotional state;
   an elated emotional state;
   a happy emotional state;
   a contented emotional state;
   a serene emotional state;
   a relaxed emotional state; and
   a calm emotional state.

27. The system for providing an interactive software system with a user experience adapted to a user's emotional state of claim 16, wherein transforming the user experience provided through the interactive software system into a user experience adapted to the predicted future emotional state of the user includes adding one or more user experience components to the user experience.

28. The system for providing an interactive software system with a user experience adapted to a user's emotional state of claim 16, wherein transforming the user experience provided through the interactive software system into a user experience adapted to the predicted future emotional state of the user includes removing one or more user experience components from the user experience.

29. The system for providing an interactive software system with a user experience adapted to a user's emotional state of claim 16, wherein the user experience adapted to the predicted future emotional state of the user is provided to the user via a user display screen displayed on a user computing system accessible by the user.

30. The system for providing an interactive software system with a user experience adapted to a user's emotional state of claim 16, wherein the emotional state data associated with a user is obtained on a periodic basis and the user experience adapted to the predicted future emotional state of the user is modified and provided to the user on a periodic basis.

31. A computer program product for using emotional state data to tailor the user experience of an interactive software system comprising:
   a nontransitory computer readable medium; and
   computer program code, encoded on the computer readable medium, comprising computer readable instructions which when executed on a processor for performing a process for using emotional state data to tailor the user experience of an interactive software system, the process for using emotional state data to tailor the user experience of an interactive software system including:

providing an interactive software system;

defining one or more user experience components, the one or more user experience components capable of combination to provide a user experience through the interactive software system, the defined user experience components including each of lengths of descriptions provided to a user and images provided to the user;

generating user experience component data, the user experience component data representing the defined one or more user experience components;

storing the user experience component data in a partitioned user experience data section of a memory device and/or system;

defining emotional state data to be obtained and analyzed;

defining emotional state threshold parameter data for each defined type of emotional state data to be obtained and analyzed;

generating emotional state threshold parameter data representing the defined emotional state threshold parameters for each defined type of emotional state data to be obtained and analyzed;

storing the emotional state threshold parameter data in a partitioned emotional state threshold parameter data section of a memory device and/or system;

providing one or more analytics modules, the one or more analytics modules implementing one or more user emotional state adaptation algorithms;

providing the one or more analytics modules access to the emotional state threshold parameter data in the partitioned emotional state threshold parameter data section of the memory device and/or system;

obtaining emotional state data associated with a user and also obtaining financial information reflecting a response to a query, the response indicating that the user is unable to accomplish a desired task associated with the query due to the user's financial condition, the obtained emotional state data being one or more of the defined one or more types of emotional state data, the emotional state data at least including data acquired by measuring muscle tension of the user;

providing the obtained emotional state data to the one or more analytics modules;

analyzing the obtained emotional state data, the emotional state parameter data associated with the one or more types of obtained emotional state data, and the financial information reflecting the response to the query;

based, at least in part, on the analysis of the obtained emotional state data the emotional state parameter data associated with the one or more types of obtained emotional state data, and the financial information reflecting the response to the query, predicting a future emotional state of the user;

based, at least in part, on the predicted future emotional state of the user, selecting a portion of the user experience component data, the selected portion of the user experience component data representing one or more selected user experience components of the defined one or more user experience components;

using the portion of the user experience component data representing one or more selected user experience components of the defined one or more user experience components to transform a user experience provided through the interactive software system into a user experience adapted to the predicted future emotional state of the user; and providing the user experience adapted to the predicted future emotional state of the user to the user.

32. The computer program product for using emotional state data to tailor the user experience of an interactive software system of claim 31, wherein the interactive software system is selected from the group of interactive software systems consisting of:

a computing system implemented tax preparation software system;
a network accessed tax preparation software system;
a web-based tax preparation software system;
a cloud-based tax preparation software system;
a computing system implemented business management software system;
a network accessed business management software system;
a web-based business management software system;
a cloud-based business management software system;
a computing system implemented accounting software system;
a network accessed accounting software system;
a web-based accounting software system;
a cloud-based accounting software system;
a computing system implemented financial management system;
a network accessed financial management system;
a web-based financial management system; and
a cloud-based financial management system.

33. The computer program product for using emotional state data to tailor the user experience of an interactive software system of claim 31, wherein the user experience is presented to the user via at least one computing system selected from the group of computing systems consisting of:

a server computing system;
a workstation;
a desktop computing system;
a mobile computing system;
a database system or storage cluster;
a virtual asset;
a switching system;
a router;
a hardware system;
a communications system;
a proxy system;
a gateway system;
a firewall system; and
a load balancing system.

34. The computer program product for using emotional state data to tailor the user experience of an interactive software system of claim 31, wherein the user experience components include at least one user experience component selected from the group of user experience components consisting of:

a sequence with which interview questions are presented to the user;
content or topics of the interview questions that are presented to the user;
font sizes used while presenting information to the user;
themes presented to the user;
types of icons displayed to the user;
types of interface formats presented to the user;
interface displays presented to the user;
images displayed to the user;

assistance resources listed and/or recommended to the user;
user recommendations presented to the user;
backgrounds presented to the user;
background audio presented to the user;
avatars and/or icons presented to the user;
highlighting mechanisms used and highlighted components presented to the user;
support mechanisms presented to the user; and
supplemental actions and recommendations presented to the user.

35. The computer program product for using emotional state data to tailor the user experience of an interactive software system of claim 31, wherein the emotional state data includes at least one of the emotional state data selected from the group of emotional state data consisting of:
   data acquired from the user's own characterization of his or her emotional state;
   data acquired from historical user data;
   data acquired from a segment of users having characteristics comparable to the user;
   data acquired from measuring the user's heart beat;
   data acquired from measuring the user's eye rotation;
   data acquired from measuring the user's perspiration;
   data acquired from measuring the user's respiration;
   data acquired from measuring the user's oxygen saturation;
   data acquired from measuring the user's blood pressure
   data acquired from measuring the user's skin temperature;
   data acquired from measuring the user's neural activity;
   data acquired from measuring the user's eye blinking;
   data acquired from measuring the user's facial expression;
   data acquired from measuring the user's voice and/or speech; and
   data acquired from measuring the user's interactions with hardware associated with an interactive software system.

36. The computer program product for using emotional state data to tailor the user experience of an interactive software system of claim 31, wherein the emotional state threshold parameters for each defined type of emotional state data to be obtained and analyzed are defined based on emotional state data associated with a general population.

37. The computer program product for using emotional state data to tailor the user experience of an interactive software system of claim 36, wherein the emotional state threshold parameters for each defined type of emotional state data to be obtained and analyzed include at least one of emotional state threshold parameter selected from the group of emotional state threshold parameters consisting of:
   a heart rate emotional state threshold parameter associated with a user's heart beat
   a heart rate variability level emotional state threshold parameter associated with a user's heart beat;
   a scan path emotional state threshold parameter associated with a user's eye rotation;
   a fixation period emotional state threshold parameter associated with a user's eye rotation;
   a skin conductance level emotional state threshold parameter associated with a user's perspiration;
   a respiration rate emotional state threshold parameter associated with a user's respiration;
   an oxygen saturation level emotional state threshold parameter associated with a user's oxygen saturation;
   a blood pressure level emotional state threshold parameter associated with a user's blood pressure;
   a skin temperature emotional state threshold parameter associated with a user's skin temperature;
   a muscle tension level emotional state threshold parameter associated with a user's muscle tension;
   a neural activity level emotional state threshold parameter associated with a user's neural activity;
   an eye blink rate emotional state threshold parameter associated with a user's eye blinking;
   a facial muscle movement emotional state threshold parameter associated with a user's facial expression;
   an acoustic characteristics emotional state threshold parameter associated with a user's voice and/or speech;
   a contact pressure emotional state threshold parameter associated with the user's interactions with hardware associated with an interactive software system; and
   a contact rate emotional state threshold parameter associated with the user's interactions with hardware associated with an interactive software system.

38. The computer program product for using emotional state data to tailor the user experience of an interactive software system of claim 31, wherein the emotional state threshold parameters for each defined type of emotional state data to be obtained and analyzed are customized based on emotional state profile data associated with the specific user.

39. The computer program product for using emotional state data to tailor the user experience of an interactive software system of claim 38, wherein the customized emotional state threshold parameters include at least one of the customized emotional state threshold parameter selected from the group of customized emotional state threshold parameters consisting of:
   a heart rate emotional state threshold parameter associated with the user's heart beat
   a heart rate variability level emotional state threshold parameter associated with the user's heart beat;
   a scan path emotional state threshold parameter associated with the user's eye rotation;
   a fixation period emotional state threshold parameter associated with the user's eye rotation;
   a skin conductance level emotional state threshold parameter associated with the user's perspiration;
   a respiration rate emotional state threshold parameter associated with the user's respiration;
   an oxygen saturation level emotional state threshold parameter associated with the user's oxygen saturation;
   a blood pressure level emotional state threshold parameter associated with the user's blood pressure;
   a skin temperature emotional state threshold parameter associated with the user's skin temperature;
   a muscle tension level emotional state threshold parameter associated with the user's muscle tension;
   a neural activity level emotional state threshold parameter associated with the user's neural activity;
   an eye blink rate emotional state threshold parameter associated with the user's eye blinking;
   a facial muscle movement emotional state threshold parameter associated with the user's facial expression;
   an acoustic characteristics emotional state threshold parameter associated with the user's voice and/or speech;
   a contact pressure emotional state threshold parameter associated with the user's interactions with hardware associated with an interactive software system; and
   a contact rate emotional state threshold parameter associated with the user's interactions with hardware associated with an interactive software system.

40. The computer program product for using emotional state data to tailor the user experience of an interactive software system of claim 31, wherein at least one of the one or more analytics modules is an interchangeable analytics module.

41. The computer program product for using emotional state data to tailor the user experience of an interactive software system of claim 31, wherein an emotional state of the user includes at least one of the emotional states selected from the group of emotional states consisting of:
- a happy emotional state or happiness;
- a sad emotional state or sadness;
- a surprised emotional state or surprise;
- a fearful emotional state or fear;
- a disgusted emotional state or disgust;
- an angry emotional state or anger;
- a tense emotional state;
- a nervous emotional state;
- a stressed emotional state;
- an upset emotional state;
- a frustrated emotional state;
- a depressed emotional state;
- a bored emotional state;
- a fatigued emotional state;
- an alert emotional state;
- an excited emotional state;
- an elated emotional state;
- a happy emotional state;
- a contented emotional state;
- a serene emotional state;
- a relaxed emotional state; and
- a calm emotional state.

42. The computer program product for using emotional state data to tailor the user experience of an interactive software system of claim 31, wherein transforming the user experience provided through the interactive software system into a user experience adapted to the predicted future emotional state of the user includes adding one or more user experience components to the user experience.

43. The computer program product for using emotional state data to tailor the user experience of an interactive software system of claim 31, wherein transforming the user experience provided through the interactive software system into a user experience adapted to the predicted future emotional state of the user includes removing one or more user experience components from the user experience.

44. The computer program product for using emotional state data to tailor the user experience of an interactive software system of claim 31, wherein the user experience adapted to the predicted future emotional state of the user is provided to the user via a user display screen displayed on a user computing system accessible by the user.

45. The computer program product for using emotional state data to tailor the user experience of an interactive software system of claim 31, wherein the emotional state data associated with a user is obtained on a periodic basis and the user experience adapted to the predicted future emotional state of the user is modified and provided to the user on a periodic basis.

\* \* \* \* \*